US008324367B2

(12) United States Patent
Kaemmerer et al.

(10) Patent No.: US 8,324,367 B2
(45) Date of Patent: *Dec. 4, 2012

(54) COMPOSITIONS AND METHODS FOR MAKING THERAPIES DELIVERED BY VIRAL VECTORS REVERSIBLE FOR SAFETY AND ALLELE-SPECIFICITY

(75) Inventors: William F. Kaemmerer, Edina, MN (US); Eric Burright, Eagan, MN (US); Deepak Ramesh Thakker, Blaine, MN (US); Jennifer Heisel, Princeton, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/580,996

(22) Filed: Oct. 16, 2009

(65) Prior Publication Data

US 2010/0284990 A1 Nov. 11, 2010

Related U.S. Application Data

(63) Continuation-in-part of application No. 11/592,812, filed on Nov. 3, 2006.

(51) Int. Cl.
C07H 21/04 (2006.01)

(52) U.S. Cl. ........... 536/24.5; 536/24.31; 536/24.1; 514/44

(58) Field of Classification Search ............ 435/6, 91.1, 435/91.31, 320.1, 462; 536/24.5
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,800,159 A | 1/1989 | Mullis et al. |
| 4,888,829 A | 12/1989 | Kleinerman et al. |
| 4,965,188 A | 10/1990 | Mullis et al. |
| 5,236,908 A | 8/1993 | Gruber et al. |
| 5,354,326 A | 10/1994 | Comben et al. |
| 5,534,350 A | 7/1996 | Liou |
| 5,624,803 A | 4/1997 | Noonberg et al. |
| 5,639,275 A | 6/1997 | Baetge et al. |
| 5,702,716 A | 12/1997 | Dunn et al. |
| 5,711,316 A | 1/1998 | Elsberry et al. |
| 5,720,720 A | 2/1998 | Laske et al. |
| 5,725,017 A | 3/1998 | Elsberry et al. |
| 5,735,814 A | 4/1998 | Elsberry et al. |
| 5,782,892 A | 7/1998 | Castle et al. |
| 5,800,390 A | 9/1998 | Hayakawa et al. |
| 5,814,014 A | 9/1998 | Elsberry et al. |
| 5,840,059 A | 11/1998 | March et al. |
| 5,882,561 A | 3/1999 | Barsoum et al. |
| 5,925,310 A | 7/1999 | Nakayama et al. |
| 5,942,455 A | 8/1999 | Barsoum et al. |
| 5,968,059 A | 10/1999 | Ellis et al. |
| 5,997,525 A | 12/1999 | March et al. |
| 6,042,579 A | 3/2000 | Elsberry et al. |
| 6,093,180 A | 7/2000 | Elsberry |
| 6,110,459 A | 8/2000 | Mickle et al. |
| 6,151,525 A | 11/2000 | Soykan et al. |
| 6,180,613 B1 | 1/2001 | Kaplitt et al. |
| 6,187,906 B1 | 2/2001 | Gluckman et al. |
| 6,231,969 B1 | 5/2001 | Knight et al. |
| 6,245,884 B1 | 6/2001 | Hook |
| 6,281,009 B1 | 8/2001 | Boyce |
| 6,291,243 B1 | 9/2001 | Fogarty et al. |
| 6,294,202 B1 | 9/2001 | Burns et al. |
| 6,300,539 B1 | 10/2001 | Morris |
| 6,309,634 B1 | 10/2001 | Bankiewicz et al. |
| 6,310,048 B1 | 10/2001 | Kumar |
| 6,313,268 B1 | 11/2001 | Hook |
| 6,319,905 B1 | 11/2001 | Mandel et al. |
| 6,343,233 B1 | 1/2002 | Werner et al. |
| 6,372,250 B1 | 4/2002 | Pardridge |
| 6,372,721 B1 | 4/2002 | Neuman et al. |
| 6,376,471 B1 | 4/2002 | Lawrence, III et al. |
| 6,436,392 B1 | 8/2002 | Engelhardt et al. |
| 6,436,708 B1 | 8/2002 | Leone et al. |
| 6,461,989 B1 | 10/2002 | El-Raghy et al. |
| 6,468,524 B1 | 10/2002 | Chiorini et al. |
| 6,551,290 B1 | 4/2003 | Elsberry et al. |
| 6,576,469 B1 | 6/2003 | Struhl et al. |
| 6,594,880 B2 | 7/2003 | Elsberry |
| 6,609,020 B2 | 8/2003 | Gill |
| 6,632,671 B2 | 10/2003 | Unger |
| 6,659,995 B1 | 12/2003 | Taheri |
| 6,870,030 B2 | 3/2005 | Powell et al. |
| 6,945,969 B1 | 9/2005 | Morris et al. |
| 7,320,965 B2 | 1/2008 | Sah et al. |
| 2001/0027309 A1 | 10/2001 | Elsberry |
| 2001/0031947 A1 | 10/2001 | Heruth |
| 2002/0004038 A1 | 1/2002 | Baugh et al. |
| 2002/0022018 A1 | 2/2002 | Curiel et al. |
| 2002/0068093 A1 | 6/2002 | Trogolo et al. |
| 2002/0114780 A1 | 8/2002 | Bankiewicz |
| 2002/0141980 A1 | 10/2002 | Bankiewicz |

(Continued)

FOREIGN PATENT DOCUMENTS

CN 2459831 Y 11/2001

(Continued)

OTHER PUBLICATIONS

Ferrer et al. Brain Research 2000, vol. 866: 257-261.*
Aebisher, Trends in Neurosci. 24(9) 553-540 (Sep. 2001).
Altschul et al., "Gapped BLAST and PSO-BLAST: a new generation of protein database search prorams," Nucl. Acids Res., 25(17): 3389-3402 (1997).
Ambion Inc., pSilencer™ 1.0-U6 siRNA Expression Vector, Catalog # 7207-20 µg, Nov. 2004, Austin, TX, 6 pgs.
Ambion Technical Bulletin #506 (as published on Nov. 16, 2002) downloaded from www.archive.org.
Ambion, Inc., Silencer siRNA® Construction Kit, Cat. #1620, Instruction Manual, Aug. 2005, 36 pgs.

(Continued)

Primary Examiner — Kimberly Chong

(57) ABSTRACT

The present invention is directed to compositions, methods and kits for regulation of gene therapies for Huntington's Disease, including, without limitation, reversible gene therapies and allele-specific therapies.

11 Claims, 4 Drawing Sheets

U.S. PATENT DOCUMENTS

| | | | |
|---|---|---|---|
| 2002/0187127 A1 | 12/2002 | Bankiewicz | |
| 2003/0022375 A1 | 1/2003 | Itoh et al. | |
| 2003/0027335 A1 | 2/2003 | Ruley et al. | |
| 2003/0032615 A1 | 2/2003 | Felgner et al. | |
| 2003/0078229 A1 | 4/2003 | Cooper et al. | |
| 2003/0088236 A1 | 5/2003 | Johnson et al. | |
| 2003/0092003 A1 | 5/2003 | Blatt et al. | |
| 2003/0095958 A1 | 5/2003 | Bhisetti et al. | |
| 2003/0109476 A1 | 6/2003 | Kmiec et al. | |
| 2003/0120282 A1 | 6/2003 | Scouten et al. | |
| 2003/0143732 A1 | 7/2003 | Fosnaugh et al. | |
| 2003/0152947 A1 | 8/2003 | Crossman | |
| 2003/0175772 A1 | 9/2003 | Wang | |
| 2003/0190635 A1 | 10/2003 | McSwiggen | |
| 2003/0224512 A1 | 12/2003 | Dobie | |
| 2004/0018520 A1 | 1/2004 | Thompson | |
| 2004/0023390 A1 | 2/2004 | Davidson | |
| 2004/0023855 A1 | 2/2004 | John et al. | |
| 2004/0186422 A1 | 9/2004 | Rioux | |
| 2004/0215164 A1 | 10/2004 | Abott | |
| 2004/0216178 A1 | 10/2004 | Jones et al. | |
| 2004/0220132 A1 | 11/2004 | Kaemmerer | |
| 2004/0258666 A1 | 12/2004 | Passini | |
| 2004/0259247 A1 | 12/2004 | Tuschl | |
| 2004/0265849 A1 | 12/2004 | Cargill | |
| 2004/0266707 A1 | 12/2004 | Leake | |
| 2005/0032733 A1 | 2/2005 | McSwiggen | |
| 2005/0042646 A1 | 2/2005 | Davidson | |
| 2005/0048641 A1 | 3/2005 | Hildebrand | |
| 2005/0096284 A1* | 5/2005 | McSwiggen | 514/44 |
| 2005/0120919 A1 | 6/2005 | Davies-Smith et al. | |
| 2005/0130919 A1 | 6/2005 | Xu et al. | |
| 2005/0137134 A1 | 6/2005 | Gill | |
| 2005/0153353 A1 | 7/2005 | Meibohm | |
| 2005/0180955 A1 | 8/2005 | Bankiewicz | |
| 2005/0202075 A1 | 9/2005 | Pardridge | |
| 2005/0209179 A1 | 9/2005 | McSwiggen | |
| 2005/0233457 A1 | 10/2005 | Block | |
| 2005/0255086 A1 | 11/2005 | Davidson | |
| 2005/0255096 A1 | 11/2005 | Poder | |
| 2005/0282198 A1 | 12/2005 | Duff | |
| 2006/0009408 A1* | 1/2006 | Davidson et al. | 514/44 |
| 2006/0014165 A1 | 1/2006 | Hackonarson | |
| 2006/0019396 A1 | 1/2006 | Hahm et al. | |
| 2006/0041242 A1 | 2/2006 | Stypulkowski | |
| 2006/0150747 A1 | 7/2006 | Mallett | |
| 2006/0178328 A1 | 8/2006 | Kaemmerer | |
| 2006/0210538 A1 | 9/2006 | Kaplitt et al. | |
| 2006/0224411 A1 | 10/2006 | Chang | |
| 2006/0228776 A1 | 10/2006 | Kaplitt et al. | |
| 2006/0248604 A1 | 11/2006 | Lewin et al. | |
| 2006/0257912 A1 | 11/2006 | Kaemmerer | |
| 2007/0031844 A1 | 2/2007 | Khvorova et al. | |
| 2007/0167389 A1 | 7/2007 | Kaemmerer | |
| 2007/0184029 A1 | 8/2007 | Mishra | |
| 2008/0060099 A1 | 3/2008 | Gordon-Kamm et al. | |
| 2008/0113351 A1 | 5/2008 | Naito | |
| 2008/0193416 A1* | 8/2008 | Federoff et al. | 424/93.2 |
| 2008/0241116 A1 | 10/2008 | Calos | |
| 2008/0241889 A1 | 10/2008 | Chesnut et al. | |
| 2008/0280843 A1 | 11/2008 | van Bilsen et al. | |
| 2009/0022864 A1 | 1/2009 | Steenhof | |
| 2009/0156503 A1 | 6/2009 | Divita et al. | |
| 2009/0165172 A1 | 6/2009 | Kausch et al. | |
| 2010/0120891 A1 | 5/2010 | Camby et al. | |

FOREIGN PATENT DOCUMENTS

| | | |
|---|---|---|
| CN | 1372322 A | 10/2002 |
| CN | 2599758 Y | 1/2004 |
| DE | 19938960 | 2/2001 |
| JP | 2004232811 | 8/2004 |
| WO | WO9220400 | 11/1992 |
| WO | WO9323569 | 11/1993 |
| WO | WO9402595 | 2/1994 |
| WO | WO9618736 | 6/1996 |
| WO | WO9740847 | 11/1997 |
| WO | WO9846273 | 10/1998 |
| WO | WO9846740 | 10/1998 |
| WO | WO9939744 | 8/1999 |
| WO | WO9950300 | 10/1999 |
| WO | WO0030567 | 6/2000 |
| WO | WO0064505 | 11/2000 |
| WO | WO0116312 | 3/2001 |
| WO | WO0149844 | 7/2001 |
| WO | WO0160794 | 8/2001 |
| WO | WO0170276 | 9/2001 |
| WO | WO0180840 | 11/2001 |
| WO | WO0191801 | 12/2001 |
| WO | WO0205804 | 1/2002 |
| WO | WO0207810 | 1/2002 |
| WO | WO0222177 | 3/2002 |
| WO | WO03042385 | 5/2003 |
| WO | 03/048298 | 6/2003 |
| WO | WO03047676 | 6/2003 |
| WO | WO03053516 | 7/2003 |
| WO | WO03070895 | 8/2003 |
| WO | WO03099298 | 12/2003 |
| WO | WO03102131 | 12/2003 |
| WO | WO2004007718 | 1/2004 |
| WO | WO2004010787 | 2/2004 |
| WO | WO2004013280 | 2/2004 |
| WO | WO2004013355 | 2/2004 |
| WO | WO2004041101 | 5/2004 |
| WO | WO2004047872 | 6/2004 |
| WO | WO2004058940 | 7/2004 |
| WO | WO2004084955 | 10/2004 |
| WO | WO2004098648 | 11/2004 |
| WO | WO2004101063 | 11/2004 |
| WO | 2005112620 A2 | 1/2005 |
| WO | WO2005027980 | 3/2005 |
| WO | 2005039643 A2 | 5/2005 |
| WO | WO2005045034 | 5/2005 |
| WO | WO2005116204 | 8/2005 |
| WO | WO2005120581 | 12/2005 |
| WO | WO2006022639 | 3/2006 |
| WO | WO2007039721 | 4/2007 |
| WO | WO2007087451 | 8/2007 |
| WO | WO2007139811 | 12/2007 |
| WO | WO2008004260 | 1/2008 |
| WO | WO2008005562 | 1/2008 |
| WO | WO2008021157 | 2/2008 |
| WO | WO2008046273 | 4/2008 |
| WO | WO2008143774 | 11/2008 |

OTHER PUBLICATIONS

Ausubel et al., Eds., Current Protocols in Molecular Biology, vols. 1-3, John Wiley & Sons, Inc., New York, NY, 1994; title page, publisher's page and table of contents only, 14 pgs.

Basi et al., "Antagonistic Effects of β-site Amyloid Precursor Protein-cleaving Enzymes 1 and 2 on β-Amyloid Peptide Production in Cells," J. Bio. Chem., Published, JBC Papers in Press, Jun. 2003; 278(34): 31512-31520.

Bass et al., Nature 411: 428-429 (2001).

Bertrand et al., Biochem Biophys Res Comm 296: 1000-1004 (2002).

Bodendorf et al., J. Neurochem. 80(5), 799-806 (Mar. 2002).

Boillée et al., "Gene therapy for ALS deliver," Trends in Neurosciences, May 2004; 27(5): 235-238.

Bortolin, Susan et al., "Analytical validation of the tag-it high-throughput microsphere-based universal array genotyping platform. Application to the multiplex detection of a panel of thrombophilia-associates single-nucleotide polymorphisms." American Association for Clinical Chemistry vol. 50(11) 2028-2036 (2004).

Brentano et al., P.N.A.S. 89:4099-4103 (1992).

Brummelkamp et al., Science 296: 550-553 (2002).

Burger et al., Mol. Ther. 10(2) 302-317 (Aug. 2004).

Cahill et al Atlas of Human Cross-Sectional Anatomy Wiley-Liss, 3rd Ed. (1995).

Cai et al., Nat. Neurosci. 4(3) 233-234 (2004).

Callahan Am. J. Pathol. 158(3) 1173-1177 (2001).

Caplen et al, Human Mol. Genet. 11(2) 175-184 (2002).

Chen et al., Nucl. Acid. Res. 20, 4581-4589 (1992).

Chi et al., "Genomewide view of gene silencing by small interfering RNAs," Proc. Natl. Acad. Sci. USA, May 2003; 100 (11): 6343-6346.

Chowhira et al., J. Biol. Chem. 269, 25856-25863 (1994).

Christman, Tissue Engineering (10) 403-409 (2004).
Cioffi et al., Biochem J. 365: 833-840 (2002).
Clark et al., Annals Int. Med. 138 400-411 (2003).
Clark et al., J. Neurosci. 17(19) 7385-7395 (1997).
Cleary et al., Nat. Neurosci. 8(1) 79-84 (ePub Dec. 19, 2004).
Couture et al., Trends in Genetics, 12(12) 510-515 (Dec. 1996).
Dai et al., Developmental Biology 285:80-90 (2005).
Davidson et al., The Lancet, Neurology 3, 145-149 (2004).
Demetriades J. Neurolog. Sci. 203-204, 247-251 (2002).
Dineley, J, Biol. Chem. 277 (25) 22768-22780 (2002).
Dorri et al., Exp. Neurology 147 48-54 (1997).
Dropulic et al., J. Virol. 66(1) 1432-1441 (1992).
During et al., "Subthalamic GAD GeneTransfer in Parkinson's Disease Patients Who Are Candidates for Deep Brain Stimulation," Human Gene Therapy, Aug. 2001; 12(12): 1587-1598.
ElBashir, EMBOJ 20(23) 6877-6888 (2001).
Ezrin-Waters et al., Can. J. Neurol. Sci. 13, 8-14 (1986).
Fu et al., Mo. Ther. 8(6) 911-917 (Dec. 2003).
Gau, Am. J. Pathol., 160(2) 731-738 (2002).
GeneDetect.com Limited, Code GD100X-RV, (GeneDetect rAVE™ gene delivery reagent), copyright 2000-2002, Auckland, New Zealand, 2 pgs.
Geraerts et al., Concise Review: Therapeutic Strategies for Parkinson Disease Based on Modulation of Adult Neurogenesis. Stem Cells, Nov. 2, 2006, vol. 25, No. 2, pp. 263-270.
Gerlai Behav. Brain Res. 95 191-203 (1998).
Glorioso, Curr. Opinion in Drug Discovery & Dev't 5(2) Pharma Press ISSN 1367-6733 (2002).
Good et al., Gene Ther. 4: 45-54 (1997).
Goto et al., Neurology, 60(5) Suppl. 1 p. A286 (Mar. 11, 2003).
Harrison et al., Mol. Cel. Neurosci. 24(3) 646-655 (2003).
Hartlage-Rubsamen et al., Glia 41(2) 169-179 (Dec. 28, 2002).
Heale et al., Nucl. Acid. Res. 22(3), 2005.
Holen et al., Nucl. Acid. Res. 30:1757-1766 (2002).
Hommel et al., "Local gene knockdown in the brain using viral-mediated RNA interference," Nature Medicine, Dec. 2003; 9(12); 1539-1544.
Hommel et al., Society for Neuroscience Abstract, 2003, Abstract 325.14 (2003).
Hooper et al., Neuroscience 63, 917-924 (1995).
Hsiao et al, Science 274 99-102(1996).
Huwyler et al., "Brain drug delivery of small molecules using immunoliposomes,"Proc. Natl. Acad., USA, Nov. 1996;93:14164-14169.
Invitrogen, pShooter™ Vector (pCMV/myc © vectors), for the intracellular targeting of recombinant proteins and antibodies, Catalog Nos. V820-20, V821-20, V822-20, V823-20, Version E, copyright 1998-2001, 35 pgs.
Invitrogen, pTRACER™-CMV2, Catalog Nos. V885-01, V885-20, Version C, copyright 1998-2001, 21 pgs.
Isacson et al., Scandinavian Physiol. Society 179 173-177 (2003).
Izant et al., Science 299 345 (1985).
Kaemmerer et al., Soc. Neurosci. Meeting (Oct. 26, 2004).
Kao et al., "BACE1 Suppression by RNA Interference in Primary Cortical Neurons," J. Bio. Chem., Published, JBC Papers in Press, Nov. 2003, 2004; 279(3): 1942-1949.
Kashani-Sabet et al., Antisense Res. Dev. 2: 3-15 (1992).
Katz et al., Bioessays 11(6): 181-185 (Dec. 1989).
Kawarabayashi et al., J. Neurosci. 372-381 (2001).
Kenderell et al., (2000) Nat. Biotech. 17, 896-898 (2000).
King et al., Physiology & Behavior, 75: 627-642, 2002.
Kitabwala et al., New England J. Med. 347(17) 1364-1367 (Oct. 24, 2002).
Kitazume J. Biol. Chem. 280(9) 8589-8595 (Mar. 4, 2005).
Klement et al., Cell 95 41-53 (1998).
L'Huillier et al., EMBO J. 11(12), 4411-4418 (1992).
Laird et al., J. Neurosci. 25, 11693-11709 (Dec. 14, 2005).
Le Gal La Salle et al, Science 259, 988-990 (1993).
Li et al., Mol. Cell Bio. 22 (5) 1277-1287 (2002).
Lisziewicz et al., Proc. Nat. Acad. Sci 90 8000-8004 (Sep. 1993).
Liu et al., Proc. Japan Academy, Series B, Physical and Biol. Sciences 79(10) 293-298 (Dec. 1993).
Luo et al., Neurobiol. Dis. 14(1), 81-88 (Oct. 2003).
Luo, Nat. Neurosci. 4, 231-232 (2001).
MacDonald, M. et al., "A novel gene containing a trinucleotide repeat that is expanded and unstable on huntington's disease chromosomes," Cell, vol. 72, 971-983 (1993).
Mas-Monteys, A. et al., "Allele-Specific silencing of mutant huntingtin for huntington's disease therapy", Molecular Therapy 13: S274-S275 (2006).
Matilla et al., J. Neurosci 18, 5508-5516 (1998).
McGarry et al., Proc. Natl Acad. Sci. 83, 399-403 (1986).
McManus et al., Nature Reviews/Genetics 3, 737-747 (Oct. 2002).
Menei et al Neurosurgery 34: 1058-1064 (1994).
Messier et al., Pharm. Biochem Behavior 63 313-318 (1999).
Miller et al Proc. Nat. Acad. Sci. 100(12) 7195-7200 (Jun. 10, 2003).
Mirus, TransIT-Neural® Transfection Reagent, Product Nos. MIR 2144, MIR 2140, MIR 2145, MIR 2146, Lit. # ML022, Rev. Mar. 2, 2005, 5 pgs.
Mirus, TransIT-TKO® Transfection Reagent, Product Nos. MIR 2154, MIR 2150, MIR 2155, MIR 2156, Lit. # ML015, Rev. Jul. 2004, 6 pgs.
Mogan et al., JECT 36: 191-196 (2004).
Morel et al., J. Comparative Neurology 387, 588-630 (1997).
Mucke et al., J. Neurosci. 20(11) 4050-4058 (Jun. 1, 2000).
Naldini et al., Proc. Nat. Acad. Sci. 93, 11382-11388 (Oct. 1996).
Noonberg et al., Nucl. Acid Res. 22(14) 2830-2836 (1994).
Noordmans et al., Soc. Neurosci. Abstr. 27, Program 572.14 (2001).
Ohkawa Nucl. Acid. Symp. Ser. 27, 15-16 (1992).
Ohno et al., "BACE1 Deficiency Rescues Memory Deficits and Cholinergic Dysfunction in a Mouse Model of Alzheimer's Disease," Neuron, Jan. 2004; 4I: 27-33.
Ojwang et al., Proc. Nat. Acad. Sci. 89 10802-10806.
Paxinos et al The Mouse Brain in Stereotactic Coordinates, Acad. Press 2nd Ed. (2001).
Potter, N. T. et al., "Technical standards and guidelines for huntington disease testing," Genetics in Medicine 6:61-65 (2004).
Promega Corporation, T4 DNA Ligase Blue/White Cloning Qualified, Part# 9PIM180, Revised Apr. 2005, 2 pgs.
Promega Corporation, T4 DNA Polymerase(a) , Part# 9PIM421, Revised May 2004, 2 pgs.
Qiagen, Qiaex II Handbook, Feb. 1999, 24 pgs.
Qiagen, Rneasy Mini Handbook, 3rd Edition, Jun. 2001, 116 pgs.
R&D Systems, β-Secretase Activity Kit, Catalog No. FP002, Aug. 2002, 2 pgs.
Roberds et al., "BACE knockout mice are healthy despite lacking the primary β-secretase activity in brain: implications for Alzheimer's disease therapeutics," Human Molecular Genetics, Jun. 2001; 10(12): 1317-1324.
Ryu, Biomaterials 26: 319-326 (2005).
Salehi et al., J. Neural Transm. 106 955-986 (1999).
Sapru et al., Annual Meeting Soc. Neurosci. Abstract 297.9, XP001204566 (2003).
Sarver et al., Science 247, 1222-1225 (1990).
Scanlon et al., Proc. Nat. Acad. Sci. 88, 10591-10595 (1995).
Schenk, "Amyloid-β immunotherapy for alzheimer's disease: the end of the beginning," Nature Reviews—Neuroscience, Oct. 2002; 3: 824-828.
Scherr et al., Cell Cycle 2(3) 251-257 (2003).
Serra et at., Medical Image Analysis 1(4) 317-329 (1996).
Singer et al., Nat. Neurosci. 8(10) 1343-1349 (ePub Aug. 28, 2005).
Stackman et al., Experimental Neurology 184, 510-520 (2003).
Strategene, AAV Helper-Free System, Instruction Manual, Catalog #240071, #240074, #240075, Revision #084007i, Aug. 2004, 50 pgs.
Strategene, pBluescript® II Phagemid Vectors, Instruction Manual, Catalog #212205, #212206, #212207, #212208, Revision #083001m, Aug. 2003, 35 pgs.
Sullenger, Science 262, p. 1566 (Dec. 3, 1993).
Taira et al., Nucl. Acid. Res. 19(19) 5125-5130 (1991).
Thompson et al., Nucl. Acid. Res. 23(12), 2259 (1995).
Timson et al., Biochem J 363:515-520 (2002).
Tuscjl Lab, "The siRNA user guide," Revised May 2004, [online]. Retrieved on Nov. 29, 2005. Retrieved from the Internet: <URL:rockefeller.edu/labheads/tuschl/sirna.html>; 6 pgs.

UI-TEI et al., "Guidelines for the selection of highly effective siRNA sequences for mammalian and chick RNA interference,"; Nucleic Acids Research (2004); vol. 32, No. 3, pp. 936-948.

Valbonesi et al., Ttransf. and Apheresis Sci. 30: 153-156 (2004).

Van Bilsen et al., "Identification and allele-specific silencing of the mutant huntingtin allele in Huntington's disease patient-derived fibroblasts," Human Gene Therapy, vol. 19, pp. 710-718 (2008).

Vassar et al., Science 286 735-741 (1999).

Ventura et al., Nucl. Acid. Res. 21(14) 3249-3255 (1993).

Vickers, Journal of Bio. Chemistry, vol. 278, No. 9 7108-7118 (2003).

Watanabe et al., J. Mol. Cel. Card. 37 (3) 691-698 (2004).

Weerasinghe et al., J. Virol. 65(10), 5531-3334 (1991).

Whitesell et al., Proc. Nat. Acad. Sci. 90: 4665-4669 (1993).

Xia et al., Nat. Biotech. 20, 1006-1010 (2002).

Xia et al., Nat. Med. 10(8) 816-820 (2004).

Yamamoto et al., Cell 101, 57-66 (2000).

Yu et al., Proc. Nat. Acad. Sci. 90 6340-6344 (1993).

Yu et al., Proc. Nat. Acad. Sci. 99 6047-6052 (2002).

Zhang et al., "Global Non-Viral Gene Transfer to the Primate Brain Following Intravenous Administration," Molecular Therapy, Jan. 2003; 7(1): 11-18.

Zhang et al., "In vivo knockdown of gene expression in brain cancer with intravenous RNAi in adult rats" J. Gene Med., 2003; 5:1039-1045; published online Aug. 4, 2003.

Zhang et al., "Intravenous RNA Interference Gene Therapy Targeting the Human Epidermal Growth Factor Receptor Prolongs Survival in Intracranial Brain Cancer," Clinical Cancer Research, Jun. 1, 2004; 10:3667-3677.

Zhang et al., 1996 J. Mol. Neurosci. 7: 13-28 (1996).

Zhao et al., J. Biol. Chem. 271(49), 31407-31411 (Dec. 1996).

Zlokovic et al., Neurosurgery 40 805-813 (1997).

Ate Loonstra et al., "Growth Inhibition and DNA Damage Induced by Cre Recombinase in Mammalian Cells", PNAS, Jul. 31, 2001, vol. 98, No. 16, pp. 9209-9214.

Qing Lin et al., "Enhanced Cell-Permeant Cre Protein for Site-Specific Recombination in Cultured Cells", BMC Biotechnology, Oct. 22, 2004, 4:25 (13 pages).

Susanne Andreas et al., "Enhanced Efficiency Through Nuclear Localization Signal Fusion on PhageΦC31-Integrase: Activity Comparison with Cre and FLPe Recombinase in Mammalian Cells", Nucleic Acids Research, 2002, vol. 30, No. 11, pp. 2299-2306.

Crooke, S.T., Annu. Rev. Med., vol. 55, pp. 61-95 (2004).

Peracchi, A. et al., Rev. Med. Virol., vol. 14, pp. 47-64 (2004).

Chirila, T. et al., Biomaterials, vol. 23, pp. 321-342 (2002).

Agrawal, S., Molecular Med. Today, vol. 6, pp. 72-81 (2000).

Opalinska, J.B. et al., Nature Rev., vol. 1, pp. 503-514 (2002).

Branch, A., Trends, in Biochem. Sci., vol. 23, pp. 45-50 (1998).

Jang et al., Expert Rev. Medical Devices, vol. 1, No. 1, pp. 127-138 (2004).

Huang et al., "High-Capacity Adenoviral Vector-Mediated Reduction of Huntingtin Aggregate Load in Vitro and In Vivo,"; Human Gene Therapy (Apr. 2007); 18:303-311.

Wang et al., "Clinico-pathological rescue of a model mouse of Huntington's disease by siRNA,"; Neuroscience Research (2005); 53:241-249.

Chang et al., "Lessons from Nature: microRNA-based shRNA libraries,"; Nature Mehthods (Sep. 2006); vol. 3, No. 9; pp. 707-714.

Du et al., Design of expression ovectors for RNA interference based on miRNAs and RNA splicing,; FEBS Journal (2006); 273: pp. 5421-5427.

Machida et al., "rAAV-mediated shRNA amerliorated neuropathology in Huntington Disease model mouse,"; BBRC (2006); 343: 190-197.

Office Action issued Mar. 16, 2011 for U.S. Appl. No. 11/592,812.

Office Action issued Oct. 5, 2010 for U.S. Appl. No. 11/592,812.

Office Action issued Jan. 25, 2010 for U.S. Appl. No. 11/592,812.

Office Action issued Jul. 29, 2009 for U.S. Appl. No. 11/592,812.

* cited by examiner

SEQUENCE LISTING

```
<160> NUMBER OF SEQ ID NOS: 133

<210> SEQ ID NO 1
<211> LENGTH: 19
<212> TYPE: RNA
<213> ORGANISM: Homo sapiens

<400> SEQUENCE: 1
aguggaugag ggagcaggc                                                 19

<210> SEQ ID NO 2
<211> LENGTH: 19
<212> TYPE: RNA
<213> ORGANISM: Homo sapiens

<400> SEQUENCE: 2
gccugcuccc ucauccacu                                                 19

<210> SEQ ID NO 3
<211> LENGTH: 19
<212> TYPE: RNA
<213> ORGANISM: Homo sapiens

<400> SEQUENCE: 3
gcacacagug gaugaggga                                                 19

<210> SEQ ID NO 4
<211> LENGTH: 19
```

```
<212> TYPE: RNA
<213> ORGANISM: Homo sapiens

<400> SEQUENCE: 4
ucccucaucc acugugugc                                                  19

<210> SEQ ID NO 5
<211> LENGTH: 19
<212> TYPE: RNA
<213> ORGANISM: Homo sapiens

<400> SEQUENCE: 5
ugaagugcac acaguggau                                                  19

<210> SEQ ID NO 6
<211> LENGTH: 19
<212> TYPE: RNA
<213> ORGANISM: Homo sapiens

<400> SEQUENCE: 6
auccacugug ugcacuuca                                                  19

<210> SEQ ID NO 7
<211> LENGTH: 19
<212> TYPE: RNA
<213> ORGANISM: Homo sapiens

<400> SEQUENCE: 7
cacacagugg augagggag                                                  19

<210> SEQ ID NO 8
<211> LENGTH: 19
<212> TYPE: RNA
<213> ORGANISM: Homo sapiens

<400> SEQUENCE: 8 cuccucauc cacugugug                                                   19

<210> SEQ ID NO 9
<211> LENGTH: 19
<212> TYPE: RNA
<213> ORGANISM: Homo sapiens

<400> SEQUENCE: 9
gcacacagua gaugaggga                                                  19

<210> SEQ ID NO 10
<211> LENGTH: 19
<212> TYPE: RNA
<213> ORGANISM: Homo sapiens

<400> SEQUENCE: 10
ucccucaucu acugugugc                                                  19

<210> SEQ ID NO 11
<211> LENGTH: 19
<212> TYPE: RNA
<213> ORGANISM: Homo sapiens

<400> SEQUENCE: 11
ugaagugcac acaguagau                                                  19

<210> SEQ ID NO 12
<211> LENGTH: 19
```

```
<212> TYPE: RNA
<213> ORGANISM: Homo sapiens

<400> SEQUENCE: 12
aucuacugug ugcacuuca                                               19

<210> SEQ ID NO 13
<211> LENGTH: 19
<212> TYPE: RNA
<213> ORGANISM: Homo sapiens

<400> SEQUENCE: 13
aguagaugag ggagcaggc                                               19

<210> SEQ ID NO 14
<211> LENGTH: 19
<212> TYPE: RNA
<213> ORGANISM: Homo sapiens

<400> SEQUENCE: 14
gccugcuccc ucaucuacu                                               19

<210> SEQ ID NO 15
<211> LENGTH: 19
<212> TYPE: RNA
<213> ORGANISM: Homo sapiens

<400> SEQUENCE: 15
cacacaguag augagggag                                               19

<210> SEQ ID NO 16
<211> LENGTH: 19
<212> TYPE: RNA
<213> ORGANISM: Homo sapiens

<400> SEQUENCE: 16 cuccccucauc uacugugug                                              19

<210> SEQ ID NO 17
<211> LENGTH: 19
<212> TYPE: RNA
<213> ORGANISM: Homo sapiens

<400> SEQUENCE: 17
ggcgcagacu uccaaaggc                                               19

<210> SEQ ID NO 18
<211> LENGTH: 19
<212> TYPE: RNA
<213> ORGANISM: Homo sapiens

<400> SEQUENCE: 18
gccuuuggaa gucugcgcc                                               19

<210> SEQ ID NO 19
<211> LENGTH: 19
<212> TYPE: RNA
<213> ORGANISM: Homo sapiens

<400> SEQUENCE: 19
cacaagggcg cagacuucc                                               19

<210> SEQ ID NO 20
<211> LENGTH: 19
```

```
<212> TYPE: RNA
<213> ORGANISM: Homo sapiens

<400> SEQUENCE: 20
ggaagucugc gcccuugug                                                  19

<210> SEQ ID NO 21
<211> LENGTH: 19
<212> TYPE: RNA
<213> ORGANISM: Homo sapiens

<400> SEQUENCE: 21
gcagggcaca agggcgcag                                                  19

<210> SEQ ID NO 22
<211> LENGTH: 19
<212> TYPE: RNA
<213> ORGANISM: Homo sapiens

<400> SEQUENCE: 22
cugcgcccuu gugcccugc                                                  19

<210> SEQ ID NO 23
<211> LENGTH: 19
<212> TYPE: RNA
<213> ORGANISM: Homo sapiens

<400> SEQUENCE: 23
acaagggcgc agacuucca                                                  19

<210> SEQ ID NO 24
<211> LENGTH: 19
<212> TYPE: RNA
<213> ORGANISM: Homo sapiens

<400> SEQUENCE: 24
uggaagucug cgcccuugu                                                  19

<210> SEQ ID NO 25
<211> LENGTH: 19
<212> TYPE: RNA
<213> ORGANISM: Homo sapiens

<400> SEQUENCE: 25
cacaagggca cagacuucc                                                  19

<210> SEQ ID NO 26
<211> LENGTH: 19
<212> TYPE: RNA
<213> ORGANISM: Homo sapiens

<400> SEQUENCE: 26
ggaagucugu gcccuugug                                                  19

<210> SEQ ID NO 27
<211> LENGTH: 19
<212> TYPE: RNA
<213> ORGANISM: Homo sapiens

<400> SEQUENCE: 27
gcagggcaca agggcacag                                                  19

<210> SEQ ID NO 28
<211> LENGTH: 19
```

```
<212> TYPE: RNA
<213> ORGANISM: Homo sapiens

<400> SEQUENCE: 28
cugugcccuu gugcccugc                                              19

<210> SEQ ID NO 29
<211> LENGTH: 19
<212> TYPE: RNA
<213> ORGANISM: Homo sapiens

<400> SEQUENCE: 29
ggcacagacu uccaaaggc                                              19

<210> SEQ ID NO 30
<211> LENGTH: 19
<212> TYPE: RNA
<213> ORGANISM: Homo sapiens

<400> SEQUENCE: 30
gccuuuggaa gucugugcc                                              19

<210> SEQ ID NO 31
<211> LENGTH: 19
<212> TYPE: RNA
<213> ORGANISM: Homo sapiens

<400> SEQUENCE: 31
acaagggcac agacuucca                                              19

<210> SEQ ID NO 32
<211> LENGTH: 19
<212> TYPE: RNA
<213> ORGANISM: Homo sapiens

<400> SEQUENCE: 32
uggaagucug ugcccuugu                                              19

<210> SEQ ID NO 33
<211> LENGTH: 19
<212> TYPE: RNA
<213> ORGANISM: Homo sapiens

<400> SEQUENCE: 33
caaugguaca gcucuuccu                                              19

<210> SEQ ID NO 34
<211> LENGTH: 19
<212> TYPE: RNA
<213> ORGANISM: Homo sapiens

<400> SEQUENCE: 34
aggaagagcu guaccauug                                              19

<210> SEQ ID NO 35
<211> LENGTH: 19
<212> TYPE: RNA
<213> ORGANISM: Homo sapiens

<400> SEQUENCE: 35
caucccaaug guacagcuc                                              19

<210> SEQ ID NO 36
<211> LENGTH: 19
```

```
<212> TYPE: RNA
<213> ORGANISM: Homo sapiens

<400> SEQUENCE: 36
gagcuguacc auugggaug                                                  19

<210> SEQ ID NO 37
<211> LENGTH: 19
<212> TYPE: RNA
<213> ORGANISM: Homo sapiens

<400> SEQUENCE: 37
ccaucccaau gguacagcu                                                  19

<210> SEQ ID NO 38
<211> LENGTH: 19
<212> TYPE: RNA
<213> ORGANISM: Homo sapiens

<400> SEQUENCE: 38
agcuguacca uugggaugg                                                  19

<210> SEQ ID NO 39
<211> LENGTH: 19
<212> TYPE: RNA
<213> ORGANISM: Homo sapiens

<400> SEQUENCE: 39
uuguggccau cccaauggu                                                  19

<210> SEQ ID NO 40
<211> LENGTH: 19
<212> TYPE: RNA
<213> ORGANISM: Homo sapiens

<400> SEQUENCE: 40
accauuggga uggccacaa                                                  19

<210> SEQ ID NO 41
<211> LENGTH: 19
<212> TYPE: RNA
<213> ORGANISM: Homo sapiens

<400> SEQUENCE: 41
caacgguaca gcucuuccu                                                  19

<210> SEQ ID NO 42
<211> LENGTH: 19
<212> TYPE: RNA
<213> ORGANISM: Homo sapiens

<400> SEQUENCE: 42
aggaagagcu guaccguug                                                  19

<210> SEQ ID NO 43
<211> LENGTH: 19
<212> TYPE: RNA
<213> ORGANISM: Homo sapiens

<400> SEQUENCE: 43
caucccaacg guacagcuc                                                  19

<210> SEQ ID NO 44
<211> LENGTH: 19
```

```
<212> TYPE: RNA
<213> ORGANISM: Homo sapiens

<400> SEQUENCE: 44
gagcuguacc guugggaug                                                    19

<210> SEQ ID NO 45
<211> LENGTH: 19
<212> TYPE: RNA
<213> ORGANISM: Homo sapiens

<400> SEQUENCE: 45
ccaucccaac gguacagcu                                                    19

<210> SEQ ID NO 46
<211> LENGTH: 19
<212> TYPE: RNA
<213> ORGANISM: Homo sapiens

<400> SEQUENCE: 46
agcuguaccg uugggaugg                                                    19

<210> SEQ ID NO 47
<211> LENGTH: 19
<212> TYPE: RNA
<213> ORGANISM: Homo sapiens

<400> SEQUENCE: 47
uuguggccau cccaacggu                                                    19

<210> SEQ ID NO 48
<211> LENGTH: 19
<212> TYPE: RNA
<213> ORGANISM: Homo sapiens

<400> SEQUENCE: 48
accguuggga uggccacaa                                                    19

<210> SEQ ID NO 49
<211> LENGTH: 19
<212> TYPE: RNA
<213> ORGANISM: Homo sapiens

<400> SEQUENCE: 49
gucggcaagc agagcuccc                                                    19

<210> SEQ ID NO 50
<211> LENGTH: 19
<212> TYPE: RNA
<213> ORGANISM: Homo sapiens

<400> SEQUENCE: 50
gggagcucug cuugccgac                                                    19

<210> SEQ ID NO 51
<211> LENGTH: 19
<212> TYPE: RNA
<213> ORGANISM: Homo sapiens

<400> SEQUENCE: 51
agccagucgg caagcagag                                                    19

<210> SEQ ID NO 52
<211> LENGTH: 19
```

```
<212> TYPE: RNA
<213> ORGANISM: Homo sapiens

<400> SEQUENCE: 52
cucugcuugc cgacuggcu                                               19

<210> SEQ ID NO 53
<211> LENGTH: 21
<212> TYPE: RNA
<213> ORGANISM: Homo sapiens

<400> SEQUENCE: 53
cagccagucg gcaagcagag c                                            21

<210> SEQ ID NO 54
<211> LENGTH: 21
<212> TYPE: RNA
<213> ORGANISM: Homo sapiens

<400> SEQUENCE: 54
gcucugcuug ccgacuggcu g                                            21

<210> SEQ ID NO 55
<211> LENGTH: 19
<212> TYPE: RNA
<213> ORGANISM: Homo sapiens

<400> SEQUENCE: 55
gucucacagc cagucggca                                               19

<210> SEQ ID NO 56
<211> LENGTH: 19
<212> TYPE: RNA
<213> ORGANISM: Homo sapiens

<400> SEQUENCE: 56
ugccgacugg cugugagac                                               19

<210> SEQ ID NO 57
<211> LENGTH: 19
<212> TYPE: RNA
<213> ORGANISM: Homo sapiens

<400> SEQUENCE: 57
gucagcaagc agagcuccc                                               19

<210> SEQ ID NO 58
<211> LENGTH: 19
<212> TYPE: RNA
<213> ORGANISM: Homo sapiens

<400> SEQUENCE: 58
gggagcucug cuugcugac                                               19

<210> SEQ ID NO 59
<211> LENGTH: 19
<212> TYPE: RNA
<213> ORGANISM: Homo sapiens

<400> SEQUENCE: 59
agccagucag caagcagag                                               19

<210> SEQ ID NO 60
<211> LENGTH: 19
```

```
<212> TYPE: RNA
<213> ORGANISM: Homo sapiens

<400> SEQUENCE: 60
cucugcuugc ugacuggcu                                            19

<210> SEQ ID NO 61
<211> LENGTH: 21
<212> TYPE: RNA
<213> ORGANISM: Homo sapiens

<400> SEQUENCE: 61
cagccaguca gcaagcagag c                                         21

<210> SEQ ID NO 62
<211> LENGTH: 21
<212> TYPE: RNA
<213> ORGANISM: Homo sapiens

<400> SEQUENCE: 62
gcucugcuug cugacuggcu g                                         21

<210> SEQ ID NO 63
<211> LENGTH: 19
<212> TYPE: RNA
<213> ORGANISM: Homo sapiens

<400> SEQUENCE: 63
gucucacagc cagucagca                                            19

<210> SEQ ID NO 64
<211> LENGTH: 19
<212> TYPE: RNA
<213> ORGANISM: Homo sapiens

<400> SEQUENCE: 64
ugcugacugg cugugagac                                            19

<210> SEQ ID NO 65
<211> LENGTH: 19
<212> TYPE: RNA
<213> ORGANISM: Homo sapiens

<400> SEQUENCE: 65
cacauacauu agcucaaac                                            19

<210> SEQ ID NO 66
<211> LENGTH: 19
<212> TYPE: RNA
<213> ORGANISM: Homo sapiens

<400> SEQUENCE: 66
guuugagcua auguaugug                                            19

<210> SEQ ID NO 67
<211> LENGTH: 19
<212> TYPE: RNA
<213> ORGANISM: Homo sapiens

<400> SEQUENCE: 67
cagcgucaca uacauuagc                                            19

<210> SEQ ID NO 68
<211> LENGTH: 19
```

```
<212> TYPE: RNA
<213> ORGANISM: Homo sapiens

<400> SEQUENCE: 68
gcuaauguau gugacgcug                                            19

<210> SEQ ID NO 69
<211> LENGTH: 19
<212> TYPE: RNA
<213> ORGANISM: Homo sapiens

<400> SEQUENCE: 69
acauacauua gcucaaacu                                            19

<210> SEQ ID NO 70
<211> LENGTH: 19
<212> TYPE: RNA
<213> ORGANISM: Homo sapiens

<400> SEQUENCE: 70
aguuugagcu aauguaugu                                            19

<210> SEQ ID NO 71
<211> LENGTH: 19
<212> TYPE: RNA
<213> ORGANISM: Homo sapiens

<400> SEQUENCE: 71
cauuagcuca aacugguug                                            19

<210> SEQ ID NO 72
<211> LENGTH: 19
<212> TYPE: RNA
<213> ORGANISM: Homo sapiens

<400> SEQUENCE: 72
caaccaguuu gagcuaaug                                            19

<210> SEQ ID NO 73
<211> LENGTH: 19
<212> TYPE: RNA
<213> ORGANISM: Homo sapiens

<400> SEQUENCE: 73
cacauacauc agcucaaac                                            19

<210> SEQ ID NO 74
<211> LENGTH: 19
<212> TYPE: RNA
<213> ORGANISM: Homo sapiens

<400> SEQUENCE: 74
guuugagcug auguaugug                                            19

<210> SEQ ID NO 75
<211> LENGTH: 19
<212> TYPE: RNA
<213> ORGANISM: Homo sapiens

<400> SEQUENCE: 75
cagcgucaca uaucagc                                              19

<210> SEQ ID NO 76
<211> LENGTH: 19
```

```
<212> TYPE: RNA
<213> ORGANISM: Homo sapiens

<400> SEQUENCE: 76
gcugauguau gugacgcug                                                  19

<210> SEQ ID NO 77
<211> LENGTH: 19
<212> TYPE: RNA
<213> ORGANISM: Homo sapiens

<400> SEQUENCE: 77
acauacauca gcucaaacu                                                  19

<210> SEQ ID NO 78
<211> LENGTH: 19
<212> TYPE: RNA
<213> ORGANISM: Homo sapiens

<400> SEQUENCE: 78
aguuugagcu gauguaugu                                                  19

<210> SEQ ID NO 79
<211> LENGTH: 19
<212> TYPE: RNA
<213> ORGANISM: Homo sapiens

<400> SEQUENCE: 79
caucagcuca aacugguug                                                  19

<210> SEQ ID NO 80
<211> LENGTH: 19
<212> TYPE: RNA
<213> ORGANISM: Homo sapiens

<400> SEQUENCE: 80
caaccaguuu gagcugaug                                                  19

<210> SEQ ID NO 81
<211> LENGTH: 19
<212> TYPE: RNA
<213> ORGANISM: Homo sapiens

<400> SEQUENCE: 81
caacaucaaa gcaucuuga                                                  19

<210> SEQ ID NO 82
<211> LENGTH: 19
<212> TYPE: RNA
<213> ORGANISM: Homo sapiens

<400> SEQUENCE: 82
ucaagaugcu uugauguug                                                  19

<210> SEQ ID NO 83
<211> LENGTH: 19
<212> TYPE: RNA
<213> ORGANISM: Homo sapiens

<400> SEQUENCE: 83
ccggccaaca ucaaagcau                                                  19

<210> SEQ ID NO 84
<211> LENGTH: 19
```

```
<212> TYPE: RNA
<213> ORGANISM: Homo sapiens

<400> SEQUENCE: 84
augcuuugau guuggccgg                                               19

<210> SEQ ID NO 85
<211> LENGTH: 19
<212> TYPE: RNA
<213> ORGANISM: Homo sapiens

<400> SEQUENCE: 85
uccggccaac aucaaagca                                               19

<210> SEQ ID NO 86
<211> LENGTH: 19
<212> TYPE: RNA
<213> ORGANISM: Homo sapiens

<400> SEQUENCE: 86
ugcuuugaug uuggccgga                                               19

<210> SEQ ID NO 87
<211> LENGTH: 19
<212> TYPE: RNA
<213> ORGANISM: Homo sapiens

<400> SEQUENCE: 87 caaguuccg gccaacauc                                                19

<210> SEQ ID NO 88
<211> LENGTH: 19
<212> TYPE: RNA
<213> ORGANISM: Homo sapiens

<400> SEQUENCE: 88
gauguuggcc ggaaacuug                                               19

<210> SEQ ID NO 89
<211> LENGTH: 19
<212> TYPE: RNA
<213> ORGANISM: Homo sapiens

<400> SEQUENCE: 89
caaaaucaaa gcaucuuga                                               19

<210> SEQ ID NO 90
<211> LENGTH: 19
<212> TYPE: RNA
<213> ORGANISM: Homo sapiens

<400> SEQUENCE: 90
ucaagaugcu uugauuuug                                               19

<210> SEQ ID NO 91
<211> LENGTH: 19
<212> TYPE: RNA
<213> ORGANISM: Homo sapiens

<400> SEQUENCE: 91
ccggccaaaa ucaaagcau                                               19

<210> SEQ ID NO 92
<211> LENGTH: 19
```

```
<212> TYPE: RNA
<213> ORGANISM: Homo sapiens

<400> SEQUENCE: 92
augcuuugau uuuggccgg                                              19

<210> SEQ ID NO 93
<211> LENGTH: 19
<212> TYPE: RNA
<213> ORGANISM: Homo sapiens

<400> SEQUENCE: 93
uccggccaaa aucaaagca                                              19

<210> SEQ ID NO 94
<211> LENGTH: 19
<212> TYPE: RNA
<213> ORGANISM: Homo sapiens

<400> SEQUENCE: 94
ugcuuugauu uuggccgga                                              19

<210> SEQ ID NO 95
<211> LENGTH: 19
<212> TYPE: RNA
<213> ORGANISM: Homo sapiens

<400> SEQUENCE: 95 caaguuccg gccaaaauc                                               19

<210> SEQ ID NO 96
<211> LENGTH: 19
<212> TYPE: RNA
<213> ORGANISM: Homo sapiens

<400> SEQUENCE: 96 gauuuggcc ggaaacuug                                               19

<210> SEQ ID NO 97
<211> LENGTH: 19
<212> TYPE: RNA
<213> ORGANISM: Homo sapiens

<400> SEQUENCE: 97
gaauuacugu ccccaucuc                                              19

<210> SEQ ID NO 98
<211> LENGTH: 19
<212> TYPE: RNA
<213> ORGANISM: Homo sapiens

<400> SEQUENCE: 98 gagauggga caguaauuc                                               19

<210> SEQ ID NO 99
<211> LENGTH: 19
<212> TYPE: RNA
<213> ORGANISM: Homo sapiens

<400> SEQUENCE: 99
gcguugaauu acugucccc                                              19

<210> SEQ ID NO 100
<211> LENGTH: 19
```

<212> TYPE: RNA
<213> ORGANISM: Homo sapiens

<400> SEQUENCE: 100
ggggacagua auucaacgc                                          19

<210> SEQ ID NO 101
<211> LENGTH: 19
<212> TYPE: RNA
<213> ORGANISM: Homo sapiens

<400> SEQUENCE: 101
agcguugaau acuguccc                                           19

<210> SEQ ID NO 102
<211> LENGTH: 19
<212> TYPE: RNA
<213> ORGANISM: Homo sapiens

<400> SEQUENCE: 102
gggacaguaa uucaacgcu                                          19

<210> SEQ ID NO 103
<211> LENGTH: 19
<212> TYPE: RNA
<213> ORGANISM: Homo sapiens

<400> SEQUENCE: 103
ucuucuagcg uugaauuac                                          19

<210> SEQ ID NO 104
<211> LENGTH: 19
<212> TYPE: RNA
<213> ORGANISM: Homo sapiens

<400> SEQUENCE: 104
guaauucaac gcuagaaga                                          19

<210> SEQ ID NO 105
<211> LENGTH: 19
<212> TYPE: RNA
<213> ORGANISM: Homo sapiens

<400> SEQUENCE: 105
gaaguacugu ccccaucuc                                          19

<210> SEQ ID NO 106
<211> LENGTH: 19
<212> TYPE: RNA
<213> ORGANISM: Homo sapiens

<400> SEQUENCE: 106 gagauggga caguacuuc                                           19

<210> SEQ ID NO 107
<211> LENGTH: 19
<212> TYPE: RNA
<213> ORGANISM: Homo sapiens

<400> SEQUENCE: 107
gcguugaagu acugucccc                                          19

<210> SEQ ID NO 108
<211> LENGTH: 19

<212> TYPE: RNA
<213> ORGANISM: Homo sapiens

<400> SEQUENCE: 108
ggggacagua cuucaacgc						19

<210> SEQ ID NO 109
<211> LENGTH: 19
<212> TYPE: RNA
<213> ORGANISM: Homo sapiens

<400> SEQUENCE: 109
agcguugaag acuguccc						19

<210> SEQ ID NO 110
<211> LENGTH: 19
<212> TYPE: RNA
<213> ORGANISM: Homo sapiens

<400> SEQUENCE: 110
gggacaguac uucaacgcu						19

<210> SEQ ID NO 111
<211> LENGTH: 19
<212> TYPE: RNA
<213> ORGANISM: Homo sapiens

<400> SEQUENCE: 111
ucuucuagcg uugaaguac						19

<210> SEQ ID NO 112
<211> LENGTH: 19
<212> TYPE: RNA
<213> ORGANISM: Homo sapiens

<400> SEQUENCE: 112
guacuucaac gcuagaaga						19

<210> SEQ ID NO 113
<211> LENGTH: 19
<212> TYPE: RNA
<213> ORGANISM: Homo sapiens

<400> SEQUENCE: 113
uagcguugaa uuacugucc						19

<210> SEQ ID NO 114
<211> LENGTH: 19
<212> TYPE: RNA
<213> ORGANISM: Homo sapiens

<400> SEQUENCE: 114
ggacaguaau ucaacgcua						19

<210> SEQ ID NO 115
<211> LENGTH: 19
<212> TYPE: RNA
<213> ORGANISM: Homo sapiens

<400> SEQUENCE: 115
uagcguugac uuacugucc						19

<210> SEQ ID NO 116
<211> LENGTH: 19

```
<212> TYPE: RNA
<213> ORGANISM: Homo sapiens

<400> SEQUENCE: 116
ggacaguaag ucaacgcua                                                19

<210> SEQ ID NO 117
<211> LENGTH: 19
<212> TYPE: RNA
<213> ORGANISM: Homo sapiens

<400> SEQUENCE: 117
uagcguugaa guacugucc                                                19

<210> SEQ ID NO 118
<211> LENGTH: 19
<212> TYPE: RNA
<213> ORGANISM: Homo sapiens

<400> SEQUENCE: 118
ggacaguacu ucaacgcua                                                19

<210> SEQ ID NO 119
<211> LENGTH: 19
<212> TYPE: RNA
<213> ORGANISM: Homo sapiens

<400> SEQUENCE: 119
uagcguugau guacugucc                                                19

<210> SEQ ID NO 120
<211> LENGTH: 19
<212> TYPE: RNA
<213> ORGANISM: Homo sapiens

<400> SEQUENCE: 120
ggacaguaca ucaacgcua                                                19

<210> SEQ ID NO 121
<211> LENGTH: 19
<212> TYPE: RNA
<213> ORGANISM: Homo sapiens

<400> SEQUENCE: 121
cacauacauu ggcucaaac                                                19

<210> SEQ ID NO 122
<211> LENGTH: 19
<212> TYPE: RNA
<213> ORGANISM: Homo sapiens

<400> SEQUENCE: 122
guuugagcca auguaugug                                                19

<210> SEQ ID NO 123
<211> LENGTH: 19
<212> TYPE: RNA
<213> ORGANISM: Homo sapiens

<400> SEQUENCE: 123
cacauacauc ggcucaaac                                                19

<210> SEQ ID NO 124
<211> LENGTH: 19
```

```
<212> TYPE: RNA
<213> ORGANISM: Homo sapiens

<400> SEQUENCE: 124
guuugagccg auguaugug                                                19

<210> SEQ ID NO 125
<211> LENGTH: 33
<212> TYPE: DNA
<213> ORGANISM: ARTIFICIAL SEQUENCE
<220> FEATURE:
<223> OTHER INFORMATION: loxP site

<400> SEQUENCE: 125
ctacttcgta tagcatacat tatacgaagt tat                                33

<210> SEQ ID NO 126
<211> LENGTH: 34
<212> TYPE: DNA
<213> ORGANISM: ARTIFICIAL SEQUENCE
<220> FEATURE:
<223> OTHER INFORMATION: loxP site

<400> SEQUENCE: 126
ataacttcgt atagcataca ttatacgaag ttat                               34

<210> SEQ ID NO 127
<211> LENGTH: 7
<212> TYPE: PRT
<213> ORGANISM: ARTIFICIAL SEQUENCE
<220> FEATURE:
<223> OTHER INFORMATION: completely synthesized

<400> SEQUENCE: 127

Cys Leu Pro Val Ala Ser Cys
1               5

<210> SEQ ID NO 128
<211> LENGTH: 7
<212> TYPE: PRT
<213> ORGANISM: ARTIFICIAL SEQUENCE
<220> FEATURE:
<223> OTHER INFORMATION: completely synthesized

<400> SEQUENCE: 128

Cys Gly Ala Arg Glu Met Cys
1               5

<210> SEQ ID NO 129
<211> LENGTH: 9
<212> TYPE: PRT
<213> ORGANISM: ARTIFICIAL SEQUENCE
<220> FEATURE:
<223> OTHER INFORMATION: completely synthesized

<400> SEQUENCE: 129

Cys Asn Ser Arg Leu His Leu Arg Cys
1               5

<210> SEQ ID NO 130
<211> LENGTH: 9
<212> TYPE: PRT
<213> ORGANISM: ARTIFICIAL SEQUENCE
<220> FEATURE:
<223> OTHER INFORMATION: completely synthesized

<400> SEQUENCE: 130
```

```
Cys Glu Asn Trp Trp Gly Asp Val Cys
1               5

<210> SEQ ID NO 131
<211> LENGTH: 21
<212> TYPE: PRT
<213> ORGANISM: ARTIFICIAL SEQUENCE
<220> FEATURE:
<223> OTHER INFORMATION: completely synthesized

<400> SEQUENCE: 131

Trp Arg Cys Val Leu Arg Glu Gly Pro Ala Gly Gly Cys Ala Trp Phe
1               5                   10                  15

Asn Arg His Arg Leu
            20

<210> SEQ ID NO 132
<211> LENGTH: 3
<212> TYPE: PRT
<213> ORGANISM: ARTIFICIAL SEQUENCE
<220> FEATURE:
<223> OTHER INFORMATION: completely synthesized

<400> SEQUENCE: 132

Arg Gly Asp
1

<210> SEQ ID NO 133
<211> LENGTH: 3
<212> TYPE: PRT
<213> ORGANISM: ARTIFICIAL SEQUENCE
<220> FEATURE:
<223> OTHER INFORMATION: completely synthesized

<400> SEQUENCE: 133

Asn Gly Ala
1
```

COMPOSITIONS AND METHODS FOR MAKING THERAPIES DELIVERED BY VIRAL VECTORS REVERSIBLE FOR SAFETY AND ALLELE-SPECIFICITY

RELATIONSHIP TO PRIOR APPLICATION

This application is a continuation-in-part of U.S. application Ser. No. 11/592,812 filed on Nov. 3, 2006, and incorporated by reference into the instant disclosure.

BACKGROUND

In gene therapy a carrier molecule called a vector must be used to deliver the therapeutic gene to the patient's target cells. Currently, the most common vector is a virus that has been genetically altered to contain therapeutic genetic sequences either to supplement expression of genes which are expressed in abnormally low levels or to inhibit expression of disease-causing genes. Target cells such as, for example, the patient's liver or lung cells are infected with the virus. The viral genome may then enter the nucleus of the cell and express the therapeutic sequence. If successful, gene therapy provides a way to fix a problem at its source. Adding a corrected copy of the gene may help the affected cells, tissues and organs work properly. Gene therapy differs from traditional drug-based approaches, which may treat the problem, but which do not repair the underlying genetic flaw.

One of the limitations of most gene therapies or vector-mediated RNA interference therapies delivered by viral or non-viral DNA vectors is that these therapies, once administered, are irreversible. Thus, the therapy could not be discontinued even if the patient were to have an unacceptable adverse reaction to the therapy. This inability for the switching gene therapy off may be detrimental or perhaps fatal to a patient.

It has been 15 years now that the Cre/lox system has been used as a way to regulate heterologous gene expression. The system begins with the cre gene, which encodes a site-specific DNA recombinase named Cre. Cre protein can recombine DNA when it locates specific sites in a DNA molecule. These sites are known as loxP sequences, which are 34 base pairs long and serve as substrates for the Cre-mediated recombination. When cells that have loxP sites in their genome also express Cre, the protein catalyzes a reciprocal recombination event between the loxP sites. Literally, the double stranded DNA is cut at both loxP sites by the Cre protein and then ligated back together. As a result, the DNA in between the loxP sites is excised and subsequently degraded.

This system has allowed researchers to create a variety of genetically modified animals and plants with the gene of their choice being externally regulated. For example, Sundaresan et al. have demonstrated that a PET reporter gene (PRG), the herpes simplex virus type 1 thymidine kinase (HSV1-tk), can be made to remain silent and can be activated by Cre-loxP-mediated recombination in cell culture and in living mice. Gene Ther., 11 (7):609-18 (2004).

Recently, scientists have begun to recognize that the Cre-loxP system and other similar systems can be used for reversible gene therapy. For example, WO2005/112620 describes a gene therapy system comprising Cre/loxP system. In their system, however, Cre is expressed in vivo. The expression of Cre in vivo often results in undesired expression of Cre due to leakage of the system. Such expression often results in unwanted genome rearrangements, and thus is unsafe for use in humans.

WO2005/039643, U.S. Patent Application Publication Nos. 20050130919, 20030022375, 20020022018, and 20040216178 also discloses either a Cre/loxP or an FLP/FRT system, but the application does not describe the use of exogenously applied Cre or use of a combination of Cre co-delivered with a cellular uptake enhancer.

U.S. Patent Application Publication No. 20030027335, discloses a Cre/loxP system with exogenously applied Cre but do not disclose that such system can be used to treat any human diseases.

Further, references fail to teach a system with multiple flanking sequences, thus failing to teach a system added precision in modulating gene as well as a safety shut-off of the system.

Thus, there continues to be a need in the for novel compositions, kits, and methods of providing and regulating treatments delivered by gene therapy.

SUMMARY OF INVENTION

This invention fulfills this and other foregoing needs by providing compositions, methods and kits for regulation of gene therapies, including, without limitation, reversible gene therapies and allele-specific therapies.

In one aspect, the invention provides a deoxyribonucleic acid sequence comprising: a first sequence, said first sequence having a 5' end and a 3' end; and a second sequence, said second sequence having a 5' end and a 3' end; and a first pair of flanking sequences, wherein a first member of the first pair is located upstream of the 5' end of the first sequence and a second member of the first pair is located downstream of the 3' end of the second sequence; and a second pair of flanking sequences, wherein a first member of the second pair is located downstream of the 3' end of a first member of the first pair and upstream of the 5' end of the first sequence; and a second member of the second pair is located downstream of the 3' end of the first sequence and upstream of the 5' end of the second sequence; wherein: one of the first sequence or the second sequence encodes a siRNA or shRNA capable of reducing mutated huntingtin and the other of the first sequence or the second sequence encodes a brain-derived neurotrophic factor (BNDF), the first sequence is excisable from said deoxyribonucleic acid sequence upon exposure of said deoxyribonucleic acid sequence to a first sequence modifier, and either: the second sequence is excisable from said deoxyribonucleic acid sequence upon exposure of said deoxyribonucleic acid sequence to a second sequence modifier, or both the first and second sequences are excisable together from the said deoxyribonucleic acid sequence upon exposure of said deoxyribonucleic acid sequence to a second sequence modifier.

In different embodiments of the invention, the first sequence modifier is different from the second sequence modifier, the first sequence modifier is selected from the group consisting of Cre recombinase, FLP recombinase, and phiC31 recombinase; and the second sequence modifier is selected from the group consisting of Cre recombinase, FLP recombinase, and phiC31 recombinase.

One of the first sequences or the second sequence may comprise a DNA sequence encoding a siRNA or shRNA useful for allele-specific treatment of Huntington's disease. Such siRNA or shRNA, is a double-stranded structure, wherein the first strand, in different embodiments, comprises one of SEQ ID NO: 1-124.

In another aspect, the invention provides a kit comprising the DNA sequence as described above, the first sequence modifier, the second sequence modifier and a set of instructions.

In different embodiments of the invention, the first sequence modifier or the second sequence modifier or both the first sequence modifier and the second sequence modifier is operably linked to a cell penetrating peptide moiety that enhances cellular uptake of the sequence modifier.

In another aspect, the invention provides method of terminating a treatment of Huntington's disease by the DNA sequence of claim 1, the method comprising administering to a subject in need thereof at least one of the first sequence modifier or the second sequence modifier.

Preferably, the first sequence modifier is different from the second sequence modifier and in different embodiments, the first and second sequence modifiers may be selected from the group consisting of Cre recombinase, FLP recombinase, and phiC31 recombinase.

Further, in different embodiments, the first sequence modifier or the second sequence modifier or both the first sequence modifier and the second sequence modifier is operably linked to a cell penetrating peptide moiety that enhances cellular uptake of the sequence modifier.

In one embodiment of the invention, the first sequence modifier and/or the second sequence modifier is administered by an intracranial injection.

DETAILED DESCRIPTION

Figure 1:
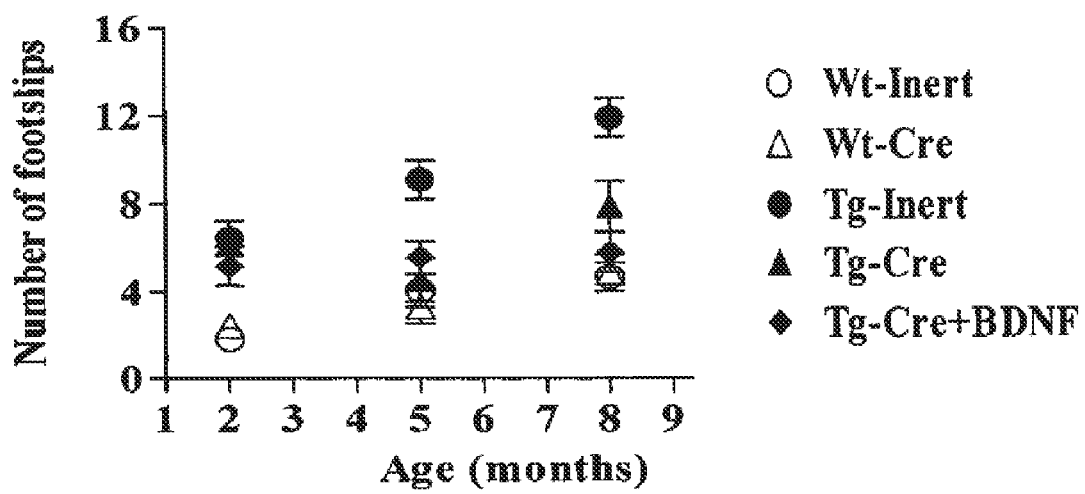
FIG. 1 illustrates improvement in the number footslips committed at five and eight months of age by transgenic (BAC-HD) mice treated at 2 months of age (1 week after behavior testing at 2 months age) with Cre or Cre+BDNF, and trained to traverse a circular beam.

For the purposes of this invention, the following non-limiting definitions are provided:

The sequence modifiers including sequence-specific DNA recombinases, including, by the way of example, at least the first sequence modifier, refer to native sequences of Cre, FLP, and ϕC31, as well as genetically engineered variants thereof, which at least partially confer recombination activity of the native proteins. Accordingly, "Cre" refers to both native Cre protein and genetically modified variants thereof, capable of recognizing loxP sites and mediating a recombination event between them, in some cases this will result in the excision of a sequence between these loxP sites.

The flanking sequences, including, by the way of example, the first member of the first pair of flanking sequences, refer to native sequences of loxP, FRT, and attB, attP, as well as genetically engineered variants thereof, which at least partially serve as a DNA recognition sequence and substrate for the recombination activity of their respective sequence modifiers. For example, other suitable lox sites include LoxB, LoxC2, LoxL and LoxR sites which are nucleotide sequences isolated from *E. coli*. Hoess et al., Proc. Natl. Acad. Sci. USA 793398 (1982). In this disclosure, all these sequences are referred to under the generic name "loxP." Accordingly, "loxP" refers to both a native and a genetically engineered sequence which is recognized by Cre, wherein Cre is capable of mediating a recombination event between a pair of the loxP sites. In some instances, this recombination will result in the excision of the DNA sequence residing between the loxP sites in the substrate DNA.

The terms "penetration enhancer", "cell penetration enhancer", and "cellular uptake enhancer:" includes single compounds as well as compositions comprising a plurality of compounds, wherein the combination of those compounds improves targeted delivery and/or cellular uptake of a sequence modifier (e.g., the first sequence modifier).

The term "functionally equivalent" sequence modifiers refers to the ability of the sequence modifiers to recognize the same flanking sequences.

The term "gene" refers to a DNA sequence that comprises control and coding sequences necessary for the production of a polypeptide or its precursor. The polypeptide can be encoded by a full length coding sequence (either genomic DNA or cDNA) or by any portion of the coding sequence so long as the desired activity is retained. In some aspects, the term "gene" also refers to an mRNA sequence or a portion thereof that directly codes for a polypeptide or its precursor.

The term "transfection" refers to the uptake of foreign DNA by a cell. A cell has been "transfected" when exogenous (i.e., foreign) DNA has been introduced inside the cell membrane. Transfection can be either transient (i.e., the introduced DNA remains extrachromosomal and is diluted out during cell division) or stable (i.e., the introduced DNA integrates into the cell genome or is maintained as a stable episomal element).

"Cotransfection" refers to the simultaneous or sequential transfection of two or more vectors into a given cell.

The term "promoter element" or "promoter" or "regulatory region" refers to a DNA regulatory region capable of being bound by an RNA polymerase in a cell (e.g., directly or through other promoter-bound proteins or substances) and allowing for the initiation of transcription of a coding or non-coding RNA sequence. A promoter sequence is, in general, bounded at its 3' terminus by the transcription initiation site and extends upstream (5' direction) to include the minimum number of bases or elements necessary to initiate transcription at any level. Within the promoter sequence may be found a transcription initiation site (conveniently defined, for example, by mapping with nuclease S1), as well as protein binding domains (consensus sequences) responsible for the binding of RNA polymerase. The promoter may be operably associated with other expression control sequences, including enhancer and repressor sequences.

The term "in operable combination", "in operable order" or "operably linked" refers to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "vector" refers to a nucleic acid assembly capable of transferring gene sequences to target cells (e.g., viral vectors, non-viral vectors, particulate carriers, and liposomes). The term "expression vector" refers to a nucleic acid assembly containing a promoter which is capable of directing the expression of a sequence or gene of interest in a cell. Vectors typically contain nucleic acid sequences encoding selectable markers for selection of cells that have been transfected by the vector. Generally, "vector construct," "expression vector," and "gene transfer vector," refer to any nucleic acid construct capable of directing the expression of a gene of interest and which can transfer gene sequences to target cells. Thus, the term includes cloning and expression vehicles, as well as viral vectors.

The term "antibody" refers to a whole antibody, both polyclonal and monoclonal, or a fragment thereof, for example a F(ab)$_2$, Fab, FV, VH or VK fragment, a single chain antibody, a multimeric monospecific antibody or fragment thereof, or a bi- or multi-specific antibody or fragment thereof. The term also includes humanized and chimeric antibodies.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols which have only a marginal effect on the patient.

The term "patient" refers to a biological system to which a treatment can be administered. A biological system can include, for example, an individual cell, a set of cells (e.g., a cell culture), an organ, a tissue, or a multi-cellular organism. A "patient" can refer to a human patient or a non-human patient.

The term "practitioner" refers to a person who uses methods, kits and compositions of the current invention on the patient. The term includes, without limitations, doctors, nurses, scientists, and other medical or scientific personnel.

The terms "miRNA molecule," "siRNA molecule," "shRNA molecule," "RNA molecule," "DNA molecule," "cDNA molecule" and "nucleic acid molecule" are each intended to cover a single molecule, a plurality of molecules of a single species, and a plurality of molecules of different species.

The term "marker sequence" refers to an amino acid sequence encoding a marker protein or a part thereof. The distinct feature of the marker protein or the part thereof is that such marker protein or the part thereof is can be visualized using routine visualization techniques. The marker protein or parts thereof include, without limitation, Green Fluorescent Protein, Red Fluorescent Protein, or β-galactosidase. Expression of these marker proteins allows direct visualization of cells in which those proteins are expressed. Further, the examples of marker proteins or parts thereof include, without limitation, a ferritin protein, a transferrin receptor protein, an iron regulatory protein, or an iron scavenger protein, or functional parts thereof capable of scavenging metal ions, as described in U.S. Patent Publication 20060024662 (Ahrens). The cells expressing those proteins can be visualized by non-invasive techniques, such as, for example, MRI.

The term "chronically implanted" with respect to a device refers to a device that remains in the body of a patient, after being positioned in a bodily tissue of the patient by a practitioner, for any period of time after the patient encounter with the practitioner is completed and the patient has departed from the presence of the practitioner.

The term "mutated huntingtin" refers to a huntingtin protein having an expanded number of CAG repeats and thereby causing a patient to have Huntington's disease. This term also refers to nucleic acid sequence (e.g., mRNA) encoding such protein.

The methods of the present invention utilize routine techniques in the field of molecular biology. Basic texts disclosing general, molecular biology methods include Sambrook et al., *Molecular Cloning, A Laboratory Manual* (3d ed. 2001) and Ausubel et al., *Current Protocols in Molecular Biology* (1994).

A person of ordinary skill in the art would recognize that deoxyribonucleic acid sequence of the present invention may be incorporated into different vectors or delivered as a naked (vectorless) DNA. The vectors suitable for hosting the deoxyribonucleic acid sequence of the present invention include, without limitations, plasmid vectors and viral vectors. Viral expression vectors are preferred, particularly those that efficiently transduce central nervous system cells (e.g., alphaviral, lentiviral, retroviral, adenoviral, adeno-associated viral (AAV)) (Williams and Koch, *Annu. Rev. Physiol.* 66:49 (2004); del Monte and Hajjar, *J. Physiol.* 546.1:49 (2003).

In one embodiment, the vector comprises an adeno associated virus (AAV), from the parvovirus family. A person of ordinary skill in the art will recognize that among the advantages of AAV are the facts that AAV is not pathogenic and that most people treated with AAV will not build an immune response to remove the virus.

Both adenoviral and AAV vectors have been shown to be effective at delivering transgenes (including transgenes directed to desired target genes) into central nervous system cells. See, e.g., Bankiewicz et al., "Long-Term Clinical Improvement in MPTP-Lesioned Primates after Gene Therapy with AAV-hAADC", Mol. Ther., E-publication Jul. 6, 2006 (A combination of intrastriatal AAV containing a nucleic sequence encoding L-amino acid decarboxylase inhibitor (AAV-hAADC) gene therapy and administration of the dopamine precursor 1-Dopa to MPTP-lesioned monkeys, resulted in long-term improvement in clinical rating scores, significantly lowered 1-Dopa requirements, and a reduction in l-Dopa-induced side effects); Machida et. al., *Biochem Biophys Res Commun*, 343(1):190-7 (2006) (Reporting a direct inhibition of mutant gene expression by rAAV-mediated delivery of RNAi into the HD model mouse striatum after the onset of disease); Mittoux at al, *J Neurosci*, 22(11): 4478-86 (2002). (Adenovirus-mediated ciliary neurotrophic factor delivery to brain resulted in increased survival of striatal neurons in response to a neurotoxin).

The deoxyribonucleic acid sequence of the present invention comprises at least one pair of flanking sequences and a first sequence located between the members of the first pair of flanking sequences. Suitable flanking sequences are those which are recognized by at least one sequence modifier. A person of ordinary skill in the art will recognize that if the at least one sequence modifier is selected from the group consisting of Cre, FLP, and ΦC31, the flanking sequences would comprise loxP, FRT, or attB/attP, respectively. The major limitation on flanking sequences is that they interact with the at least one sequence modifier resulting in removal of a sequence between the flanking sequences (e.g., the first sequence).

In different embodiments of the invention, the deoxyribonucleic acid sequence may comprise more than one pair of flanking sequences, such as, for example, a first pair of flanking sequences and a second pair of flanking sequences.

A person of ordinary skill in the art will appreciate that at least two arrangements of these pairs of the flanking sequences are possible. In one arrangement, the members of one of flanking sequences (for example, the first pair) are located outside of a sequence defined by a 5' end of the first member of at least the second pair of flanking sequences and a 3' end of the second member of at least the second pair of flanking sequences. In this embodiment, addition of one sequence modifier (for example, the first sequence modifier) will not result in removal of the second sequence (which is located between the members of the at least the second pair of the flanking sequences). By the same logic, addition of the second sequence modifier will not result in removal of the first sequence, which is located between the (embers of the first pair of flanking sequences. This arrangement is advantageous for allele therapy, as discussed below.

In another arrangement, the deoxyribonucleic acid sequence comprises a first sequence, said first sequence having a 5' end and a 3' end; a second sequence, said second sequence having a 5' end and a 3' end; a first pair of flanking sequences, wherein a first member of the first pair is located upstream of the 5' end of the first sequence and a second member of the first pair is located downstream of the 3' end of the second sequence; and a second pair of flanking sequences, wherein a first member of the second pair is located downstream of the 3' end of a first member of the first pair and upstream of the 5' end of the first sequence; and a second member of the second pair is located downstream of the 3' end of the first sequence and upstream of the 5' end of the second sequence This arrangement provides an emergency shut-off: administration of the first sequence modifier will result in removal of the both first and the second sequences.

The sequences between the members of the pair or pairs of flanking sequences preferably encode for bioactive molecules. These bioactive molecules may be designed according to the needs of the gene therapy. For example, if the practitioner desires to block the expression of a target gene expressed in the target area, suitable sequences for bioactive molecule will encode for miRNA, or shRNA, or siRNA. In one embodiment, the target area is located within the central nervous system of the patient, e.g., the brain or cerebrospinal fluid. In such embodiment, the target genes include, without limitation, IT15/HD, DRPLA, SCA1, SCA2, SCA3/MJD, SCA7, BACE1, and SNCA/alpha-synuclein.

On the other hand, if the practitioner desires to supplement the expression of the target gene, suitable sequences for the bioactive molecule will encode for the protein encoded by the target gene. For example, if the target area is located within the central nervous system, different enzymes or other types of proteins may be produced. In one embodiment, the protein is hexosaminidase A. In additional embodiments, the sequences between the members of the pair or pairs of flanking sequences may comprise marker sequences.

A person of the ordinary skill in the art will appreciate that brain is not the only target area to which the systems, methods and kits of the instant invention can be administered. Another non-limiting example of the target area suitable to be treated with the systems, methods and kits of the instant is myocardium. In such embodiment, the target genes include, without limitation, phospholamban, SERCA2a, Kir2.1, KCNJ2, HCN2, and HCN4, The design and use of small interfering RNA complementary to mRNA targets that produce particular proteins is a recent tool employed by molecular biologists to prevent translation of specific mRNAs. Various groups have been recently studying the effectiveness of siRNAs as biologically active agents for suppressing the expression of specific proteins involved in neurological disorders. For example, Caplen et al. (*Human Molecular Genetics,* 11(2): 175-184 (2002)) assessed a variety of different double stranded RNAs for their ability to inhibit cell expression of mRNA transcripts of the human androgen receptor gene containing different CAG repeat lengths. Their work found gene-specific inhibition occurred with double stranded RNAs containing CAG repeats only when flanking sequences to the CAG repeats were present in the double stranded RNAs. They were also able to show that constructed double stranded RNAs were able to rescue caspase-3 activation induced by expression of a protein with an expanded polyglutamine region. (Xia, Mao, et al., *Nature Biotechnology,* 20: 1006-1010 (2002)) demonstrated the inhibition of polyglutamine (GAG) expression in engineered neural PC12 clonal cell lines that express a fused polyglutamine-fluorescent protein using constructed recombinant adenovirus expressing shRNAs targeting the mRNA encoding green fluorescent protein.

One aspect of the present invention provides an siRNA molecule corresponding to at least a portion of a target gene siRNAs are typically short (19-29 nucleotides), double-stranded RNA molecules that cause sequence-specific degradation of complementary target mRNA in a process known as RNA interference (RNAi) (Bass, *Nature* 411-428 (2001)).

Accordingly, in some embodiments, the siRNA molecules comprise a double-stranded structure comprising a sense strand and an antisense strand, wherein the antisense strand comprises a nucleotide sequence that is complementary to at least a portion of a desired nucleic acid sequence and the sense strand comprises a nucleotide sequence that is complementary to at least a portion of the nucleotide sequence of said antisense region, and wherein the sense strand and the antisense strand each comprise about 19-29 nucleotides.

Any desired nucleic acid sequence can be targeted by the siRNA molecules of the present invention. Nucleic acid sequences encoding desired gene targets are publicly available from Genbank. In one embodiment, an siRNA molecule corresponds to at least a portion of a gene containing an SNP variant of an allele in a heterozygous subject that is on the same mRNA transcript as a disease-causing mutation located at a remote region of the gene's mRNA, wherein Such siRNA nucleic acid sequence is capable of inhibiting translation of the mRNA for the allele containing the disease-causing mutation in a cell. This embodiment is particularly suitable for allele-specific therapy as described below.

The siRNA molecules targeted to desired sequence can be designed based on criteria well known in the art (e.g., Elbashir et al., *EMBO J.* 20:6877 (2001)). For example, the target segment of the target mRNA preferably should begin with AA (most preferred), TA, GA, or CA; the GC ratio of the siRNA molecule preferably should be 45-55%; the siRNA molecule preferably should not contain three of the same nucleotides in a row; the siRNA molecule preferably should not contain seven mixed G/Cs in a row; the siRNA molecule preferably should comprise two nucleotide overhangs (preferably TT) at each 3' terminus; the target segment preferably should be in the ORF region of the target mRNA and preferably should be at least 75 bp after the initiation ATG and at least 75 bp before the stop codon; and the target segment preferably should not contain more than 16-17 contiguous base pairs of homology to other coding sequences.

Based on some or all of these criteria, siRNA molecules targeted to desired sequences can be designed by one of skill in the art using the aforementioned criteria or other known criteria (e.g., Gilmore et al., *J. Drug Targeting* 12:315 (2004); Reynolds et al., *Nature Biotechnol.* 22:326 (2004); Ui-Tei et al., *Nucleic Acids Res.*, 32:936 (2004)). Such criteria are available in various web-based program formats useful for designing and optimizing siRNA molecules siDESIGN Center at Dharmacon; BLOCK-iT RNAi Designer at Invitrogen; siRNA Selector at Wistar Institute; siRNA Selection Program at Whitehead Institute; siRNA Design at Integrated DNA Technologies; siRNA Target. Finder at Ambion; and siRNA Target Finder at Genscript).

Short hairpin RNA (shRNA) molecules fold back on themselves to produce the requisite double-stranded portion (Yu et al., *Proc. Natl. Acad. Sci. USA* 99:6047 (2002)). Such single-stranded RNA molecules can be produced using DNA templates (e.g., Yu et al., *Proc. Natl. Acad. Sci. USA* 99:6047 (2002)).

In another embodiment, the present invention may be used for allele-specific therapy. For example, it has long been known that Huntington disease is a dominant-negative disease caused by an increased number of the CAG repeats at the 5' end of the mRNA. It is also known that a single mutant copy of the gene is sufficient to cause the disease, and that a single nonmutant copy of the gene is sufficient for normal neuronal development and function. It is further known that the Huntington gene, IT15, has many Single Nucleotide Polymorphisms downstream of the CAG repeats. As disclosed in a Previously submitted application, it is possible to diagnose which variant of SNP in the Huntington gene corresponds to (that is, is part of the same molecule as) the allele containing the pathologically increased number of CAG repeats (See U.S. patent application Ser. No. 11/439,858, filed on May 24, 2006, which is incorporated herein by reference in its entirety). That application also disclosed the use of siRNA for allele-specific treatment of Huntington's and other diseases. Thus, one embodiment of the instant invention takes a step further in this embodiment, the first and the second sequences may encode for shRNAs or siRNAs of different SNP variants of the Huntington's Disease gene, and when the practitioner, using the allele-specific diagnosis disclosed in an earlier application, finds which SNP variant co-segregates with the disease-causing mutation, it would be possible to remove the sequence targeting the non-mutated (or wildtype) allele.

Thus, for example, if the siRNA or shRNA is for reducing a mutated huntingtin, the following non-limiting exemplary sequences may be used (the SNP nucleotide is in bold):

TABLE 1 sequences useful for alleles-specific huntingtin inhibition

| SEQ ID No | SEQUENCE |
|---|---|
| 1 | 5'-aguggaugagggagcaggc-3' |
| 2 | 5'-gccugcucccucauccacu-3' |
| 3 | 5'-gcacacaguggaugaggga-3' |
| 4 | 5'-ucccucauccacuguguge-3' |
| 5 | 5'-ugaagugcacacaguggau-3' |
| 6 | 5'-auccacugugugcacuuca-3' |
| 7 | 5'-cacacaguggaugagggag-3' |
| 8 | 5'-cucccucauccacugugug-3' |

TABLE 1-continued sequences useful for alleles-specific huntingtin inhibition

| SEQ ID No | SEQUENCE |
|---|---|
| 9 | 5'-gcacacaguagaugaggga-3' |
| 10 | 5'-ucccucaucuacugugugc-3' |
| 11 | 5'-ugaagugcacacaguagau-3' |
| 12 | 5'-aucuacugugugcacuuca-3' |
| 13 | 5'-aguagaugagggagcaggc-3' |
| 14 | 5'-gccugcucccucaucuacu-3' |
| 15 | 5'-cacacaguagaugagggag-3' |
| 16 | 5'-cucccucaucuacugugug-3' |
| 17 | 5'-ggcgcagacuuccaaaggc-3' |
| 18 | 5'-gccuuuggaagucugcgcc-3' |
| 19 | 5'-cacaagggcgcagacuucc-3' |
| 20 | 5'-ggaagucugcgcccuugug-3' |
| 21 | 5'-gcagggcacaagggcgcag-3' |
| 22 | 5'-cugcgcccuugugcccugc-3' |
| 23 | 5'-acaagggcgcagacuucca-3' |
| 24 | 5'-uggaagucugcgcccuugu-3' |
| 25 | 5'-cacaagggcacagacuucc-3' |
| 26 | 5'-ggaagucugugcccuugug-3' |
| 27 | 5'-gcagggcacaagggcacag-3' |
| 28 | 5'-cugugcccuugugcccugc-3' |
| 29 | 5'-ggcacagacuuccaaaggc-3' |
| 30 | 5'-gccuuuggaagucugugcc-3' |
| 31 | 5'-acaagggcacagacuucca-3' |
| 32 | 5'-uggaagucugugcccuugu-3' |
| 33 | 5'-caaugguacagcucuuccu-3' |
| 34 | 5'-aggaagagcuguaccauug-3' |
| 35 | 5'-caucccaaugguacagcuc-3' |
| 36 | 5'-gagcuguaccauugggaug-3' |
| 37 | 5'-ccaucccaaugguacagcu-3' |
| 38 | 5'-agcuguaccauugggaugg-3' |
| 39 | 5'-uuguggccaucccaauggu-3' |
| 40 | 5'-accauugggauggccacaa-3' |
| 41 | 5'-caacgguacagcucuuccu-3' |
| 42 | 5'-aggaagagcuguaccguug-3' |
| 43 | 5'-caucccaacgguacagcuc-3' |
| 44 | 5'-gagcuguaccguugggaug-3' |
| 45 | 5'-ccaucccaacgguacagcu-3' |
| 46 | 5'-agcuguaccguugggaugg-3' |

TABLE 1-continued sequences useful for alleles-specific huntingtin inhibition

| SEQ ID No | SEQUENCE |
|---|---|
| 47 | 5'-uuguggccaucccaacggu-3' |
| 48 | 5'-accguugggauggccacaa-3' |
| 49 | 5'-gucggcaagcagagcuccc-3' |
| 50 | 5'-gggagcucugcuugccgac-3' |
| 51 | 5'-agccagucggcaagcagag-3' |
| 52 | 5'-cucugcuugccgacuggcu-3' |
| 53 | 5'-cagccagucggcaagcagagc-3' |
| 54 | 5'-gcucugcuugccgacuggcug-3' |
| 55 | 5'-gucucacagccagucggca-3' |
| 56 | 5'-ugccgacuggcugugagac-3' |
| 57 | 5'-gucagcaagcagagcuccc-3' |
| 58 | 5'-gggagcucugcuugcugac-3' |
| 59 | 5'-agccagucagcaagcagag-3' |
| 60 | 5'-cucugcuugcugacuggcu-3' |
| 61 | 5'-cagccagucagcaagcagagc-3' |
| 62 | 5'-gcucugcuugcugacuggcug-3' |
| 63 | 5'-gucucacagccagucagca-3' |
| 64 | 5'-ugcugacuggcugugagac-3' |
| 65 | 5'-cacauacauuagcucaaac-3' |
| 66 | 5'-guuugagcuaauguaugug-3' |
| 67 | 5'-cagcgucacauacauuagc-3' |
| 68 | 5'-gcuaauguaugugacgcug-3' |
| 69 | 5'-acauacauuagcucaaacu-3' |
| 70 | 5'-aguuugagcuaauguaugu-3' |
| 71 | 5'-cauuagcucaaacugguug-3' |
| 72 | 5'-caaccaguuugagcuaaug-3' |
| 73 | 5'-cacauacaucagcucaaac-3' |
| 74 | 5'-guuugagcugauguaugug-3' |
| 75 | 5'-cagcgucacauacaucagc-3' |
| 76 | 5'-gcugauguaugugacgcug-3' |
| 77 | 5'-acauacaucagcucaaacu-3' |
| 78 | 5'-aguuugagcugauguaugu-3' |
| 79 | 5'-caucagcucaaacugguug-3' |
| 80 | 5'-caaccaguuugagcugaug-3' |
| 81 | 5'-caacaucaaagcaucuuga-3' |
| 82 | 5'-ucaagaugcuuugauguug-3' |
| 83 | 5'-ccggccaacaucaaagcau-3' |
| 84 | 5'-augcuuugauguuggccgg-3' |
| 85 | 5'-uccggccaacaucaaagca-3' |
| 86 | 5'-ugcuuugauguuggccgga-3' |
| 87 | 5'-caaguuccggccaacauc-3' |
| 88 | 5'-gauguuggccggaaacuug-3' |
| 89 | 5'-caaaaucaaagcaucuuga-3' |
| 90 | 5'-ucaagaugcuuugauuug-3' |
| 91 | 5'-ccggccaaaaucaaagcau-3' |
| 92 | 5'-augcuuugauuuggccgg-3' |
| 93 | 5'-uccggccaaaaucaaagca-3' |
| 94 | 5'-ugcuuugauuuggccgga-3' |
| 95 | 5'-caaguuccggccaaaauc-3' |
| 96 | 5'-gauuuggccggaaacuug-3' |
| 97 | 5'-gaauuacuguccccaucuc-3' |
| 98 | 5'-gagauggggacaguaauuc-3' |
| 99 | 5'-gcguugaauuacuguccc-3' |
| 100 | 5'-ggggacaguaauucaacgc-3' |
| 101 | 5'-agcguugaauuacugucc-3' |
| 102 | 5'-gggacaguaauucaacgcu-3' |
| 103 | 5'-ucuucuagcguugaauuac-3' |
| 104 | 5'-guaauucaacgcuagaaga-3' |
| 105 | 5'-gaaguacugucccaucuc-3' |
| 106 | 5'-gagauggggacaguacuuc-3' |
| 107 | 5'-gcguugaaguacuguccc-3' |
| 108 | 5'-ggggacaguacuucaacgc-3' |
| 109 | 5'-agcguugaaguacugucc-3' |
| 110 | 5'-gggacaguacuucaacgcu-3' |
| 111 | 5'-ucuucuagcguugaaguac-3' |
| 112 | 5'-guacuucaacgcuagaaga-3' |
| 113 | 5'-uagcguugaauuacugucc-3' |
| 114 | 5'-ggacaguaauucaacgcua-3' |
| 115 | 5'-uagcguugacuuacugucc-3' |
| 116 | 5'-ggacaguaagucaacgcua-3' |
| 117 | 5'-uagcguugaaguacugucc-3' |
| 118 | 5'-ggacaguacuucaacgcua-3' |
| 119 | 5'-uagcguugauguacugucc-3' |
| 120 | 5'-ggacaguacaucaacgcua-3' |
| 121 | 5'-cacauacauuggcucaaac-3' |

TABLE 1-continued sequences useful for
alleles-specific huntingtin inhibition

| SEQ ID No | SEQUENCE |
|---|---|
| 122 | 5'-guuugagccaauguaugug-3' |
| 123 | 5'-cacauacaucggcucaaac-3' |
| 124 | 5'-guuugagccgauguaugug-3' |

These and other sequences useful for this invention were discovered by inventors and published in a PCT application PCT/US2008/064532 published as WO/20081147837 and incorporated herein by reference in its entirety.

Alternatively, the first and the second sequences may contain the bioactive molecules modifying the expression of the target gene to different degrees. Thus, if the effect of the gene therapy is stronger than desired, the practitioner may decide to remove one of the sequences coding for one of the bioactive molecules by administering the appropriate sequence modifier.

A person of ordinary skill in the art will recognize that the sequences, such as the first sequence and the second sequence may encode for more than only one bioactive molecule. For example, the practitioner may design the deoxyribonucleic acid sequence of the present invention in such as way that one sequence, e.g., the first sequence, contains an internal ribosome entry site, or IRES. The methods of including IRES into the first sequence are well known in the art and described, for example, in Osti D. et al., J Viral Methods. 2006 May 9.

A person of ordinary skill in the art will further recognize that in some embodiments, it is advantageous to put the first and/or the second sequences under control of the first and/or the second promoters, or regulatory sequences, respectively. The regulatory sequences may comprise a basic promoter, such as, for example, a TATA box within 20-30 bases from the start of transcription of the bioactive molecule. Further, the regulatory sequence may comprise an enhancer located within or outside of the sequence defined by the first and the second pair of the first flanking sequence and/or at least the second pair of the flanking sequences. In one embodiment, the regulatory sequence may comprise highly and constitutively active promoters. Suitable eukaryotic promoters include constitutive RNA polymerase II promoters (e.g., cytomegalovirus (CMV) promoter, the SV40 early promoter region, the promoter contained in the 3' long terminal repeat of Rous sarcoma virus (RSV), the herpes thymidine kinase (TK) promoter, and the chicken beta-actin promoter), and RNA polymerase III promoters (e.g., U6, H1, 7SK and 7SL). The person of ordinary skill will recognize that the sequences of these promoters are well known in the art.

In yet another embodiment, the regulatory sequences may be organ and/or tissue specific promoters. In this embodiment, the first and/or at least the second bioactive molecule will be expressed essentially in the cells which have the proper pool of transcription factors. By way of example, Mellon at al, was able to develop clonal, differentiated, neurosecretory cell line comprising hypothalamic neurons secreting gonadotropin release factor by creating transgenic mice comprising SV40 T-antigen oncogene under control of GnRH regulatory region. Neuron, 5(1):1-10 (1990).

The at least partially reversible gene therapy system of the present invention may be constructed by methods generally known to persons of ordinary skill in the art and described, for example, in Sambrook et al., *Molecular Cloning, A Laboratory Manual* (3d ed. 2001) and Ausubel et al., *Current Protocols in Molecular Biology* (1994). Further, the at least partially reversible gene therapy system of the present invention may be produced by multiple methods, most notably, by using packaging cell strains such as, for example, those described in J. M. Coffin, S. H. Hughes & H. E. Varmus (eds.), Retroviruses, Cold Spring Harbor Laboratory Press. Other methods for producing retroviruses and for infecting cells in vitro or in vivo are described in Current. Protocols in Molecular Biology, Ausubel, F. M. et al. (eds.) Greene Publishing Associates, (1989), Sections 9.10-9.14.

In another aspect, the invention comprises methods of providing at least partially reversible gene therapy. In different embodiments, the method comprises accessing the target area within the patient's body with a delivery device and delivering at a first time a deoxyribonucleic acid sequence according to the systems of the present invention, as described above. Further, the method comprises, the step of delivering an appropriate sequence modifier at a second, later time. In one embodiment, e.g., where the deoxyribonucleic acid comprises the first and the second sequences, the method may further comprise delivering another sequence modifier at a third time, which is after the second time. For example, in one embodiment, delivering the first sequence modifier at the second time may be useful for regulating the amount of a protein encoded by one of the sequences, e.g., the first sequence. In one embodiment, the administering of the first sequence modifier will not affect the expression of the second sequence. When the course of the treatment is complete (e.g., at the third time), the second sequence modifier may be administered to the target area to remove the second sequence.

In one embodiment, the delivery device comprises a catheter. Preferably, the catheter is implantable. A person of the ordinary skill in the art will appreciate that such catheter may stay in the target area between the first and the second (and if necessary, the third) times, which will decrease trauma from the placement of the catheter and minimize a possibility that the sequence modifier will be delivered to an area different from the target area.

In one embodiment, the target area is within the central nervous system, the patient's brain. In this embodiment, the catheter may comprise an intracranial access catheter. The catheter will have a distal tip, which can be placed either in the parenchymal tissue of the brain or within a cerebral ventricle.

The target area may be located by many methods. For example, for some application, the targeted area may be located by stereotactical or gross anatomical atlases. In other embodiments, when the precise location of the targeted area is crucial, e.g., when the at least partially reversible gene therapy system is delivered into the brain of the patient, other mapping means may be used. Such mapping means include, without limitation, Positron Emission Tomography and Single Photon Emission Computed Tomography (PET and SPECT, respectively), pharmacological Magnetic Resonance Imaging (PhMRI), functional MRI (fMRI), and contrast-enhanced computerized tomography (CT) scan.

In another embodiment, Computer-aided atlas-based functional neurosurgery methodology can be used to accurately and precisely inject the deoxyribonucleic acid of the present invention. Such methodologies permit three-dimensional display and real-time manipulation of cerebral structures. Neurosurgical planning with mutually Preregistered multiple brain atlases in all three orthogonal orientations is therefore possible and permits increased accuracy of target definition for treatment injection or implantation, reduced time of the surgical procedure by decreasing the number of tracts, and facilitates planning of more sophisticated, trajectories. See e.g. Nowinski W. L. et al., Computer-Aided Stereotactic Functional Neurosurgery Enhanced by the Use of the Multiple Brain Atlas Database, IEEE Trans Med Imaging 19(1); 62-69:2000.

Following introduction of the deoxyribonucleic acid of the present invention into cells, changes in desired gene product levels can be measured if desired. Desired gene products include, for example, desired mRNA and desired polypeptide, and both can be measured using methods well-known to those skilled in the art. For example, desired mRNA can be directly detected and quantified using, e.g., Northern hybridization, in situ hybridization, dot and slot blots, or oligonucleotide arrays, or can be amplified before detection and quantitation using, e.g., polymerase chain reaction (PCR), reverse-transcription-PCR (RT-PCR), PCR-enzyme-linked immunosorbent assay (PCR-ELISA), or ligase chain reaction (LCR).

Desired polypeptides (or fragments thereof) can be detected and quantified using various well-known immunological assays, such as, e.g., enzyme-linked immunosorbent assay (ELISA), radioimmunoassay (RIA), immunoprecipitation, immunofluorescence, and Western blotting. Antibodies that recognize the polypeptide epitopes (preferably the human epitopes) are commercially available for use in immunological assays from, e.g., EMD Biosciences (San Diego, Calif.), Upstate (Charlottesville, Va.), Abeam (Cambridge, Mass.), Affinity Bioreagents (Golden, Colo.) and Novus Biologicals (Littleton, Colo.), or may be produced by methods well-known to those skilled in the art.

A person of ordinary skill in the art will also appreciate that the invention discloses a method of stopping or at least partially reversing the gene therapy. In different embodiments, the method comprises delivering an effective amount of at least one sequence modifier, wherein the at least one sequence modifier is selected from the group consisting of the first sequence modifier, the second sequence modifier, and a combination thereof. The identity of the sequence modifier can be determined on the basis of the flanking sequences surrounding the sequence encoding a bioactive molecule, e.g., the first bioactive molecule, or the second bioactive molecule. For example, if the deoxyribonucleic acid has only the loxP flanking sequences, then the sequence modifier is Cre. On the other hand, if the deoxyribonucleic acid sequence has both loxP and an attB/attP pair of flanking sequences, the sequence modifier is selected from the group consisting of Cre, ΦC31 and a combination thereof.

A person of ordinary skill in the art will appreciate that the sequence modifier can be genetically engineered.

In one embodiment, the practitioner may choose to associate the sequence modifier with a cell penetrating peptide moiety that enhances cellular uptake of the sequence modifier. For example, the art has shown that a peptide comprising RGD or NGA sequences can target at least one sequence modifier to tumors. See, for example, Pasqualini et al., Nat. Biotechnol. 15(6):542-546 (1997) and U.S. Patent Pub. 20040258747 (Ponzoni). Accordingly, such modification of the sequence modifier would be beneficial for the partially reversible gene therapy which is to be expressed in neovascularized tissues, such as, for example, tumors, or painful intervertebral disks. Further, amino acid sequence CLPVASC (SEQ ID NO: 127) and CGAREMC (SEQ ID NO: 128) are kidney-specific homing peptides, while sequences CNSRLHLRC (SEQ ID NO: 129), CENWWGDVC (SEQ ID NO: 130), WRCVLREGPAGGCAWFNRHRL (SEQ ID NO: 131) are brain-specific homing peptides. U.S. Patent Pub. 20050037417 (Ruoslahti). Thus, in different embodiments of the invention, the sequence modifier is modified with a cell and/or tissue-specific homing sequence which is a peptide comprising an amino acid sequence selected from the group consisting of RGD (SEQ ID NO: 132), NGA (SEQ ID NO: 133), CLPVASC (SEQ ID NO: 127), CENWWGDVC (SEQ ID NO: 130), CGAREMC (SEQ ID NO: 128), CNSRLHLRC (SEQ ID NO: 129), WRCVLREGPAGGCAWFNRHRL (SEQ ID NO: 131), and a combination thereof. The methods of genetic engineering useful for modification of the sequence modifier are well known in the art and described, for example, in Andreas et al. (2002), Sambrook et al., Molecular Cloning, A Laboratory Manual (3d ed. 2001) and Ausubel et al., Current Protocols in Molecular Biology (1994).

Methods of producing the sequence modifier are well known in the art. These methods include, without limitation, chemical synthesis and production of the recombinant at least one sequence modifier in expression systems.

For example, an expression vector for the preparation of the sequence modifier may be a mammal-derived expression vector (for example, pcDNA3 (Invitrogen), pEGF-BOS (Nucleic Acids. Res. 18(17):5322, 1990), pEF, and pCDM8); an insect cell-derived expression vector (for example, "Bac-to-BAC baculovirus expression system" (GIBCO BRL), pBacPAK8); a plant-derived expression vector (for example, pMH1 and pMH2); an animal virus-derived expression vector (for example, pHSV, pMV, and pAdexLcw); a retrovirus-derived expression vector (for example, pzlpneo); a yeast-derived expression vector (for example, "Pichia Expression Kit" (Invitrogen), pNV11, and SP-Q01); or a *Bacillus subtilis*-derived expression vectors (for example, pPL600 and pKTH0), other than *E. coli*. Also see Colley et al., J. Biol. Chem. 264:17619-17622 (1989); Guide to Protein Purification, in Methods in Enzymology, vol. 12 (Deutscher, ed., 1990). The sequence modifier can be purified from the expression system by any method known in the art, including without limitation, the methods described in U.S. Patent. Application Publication No. 2005011804 (Lorens).

For the expression in animal cells, such as CHO, COS, and NIH3T3 cells, the expression vector must have a promoter such as the SV40 promoter (Mulligan et al., Nature 277:108, 1979), MMLV-LTR promoter, the EF1α promoter (Mizushima et al., Nucleic Acids Res. 18:5322, 1990), or the CMV promoter. More preferably, the vector may contain a marker gene for the selection of transformants (for example, a drug resistance gene for selection by a drug such as neomycin and G418). Such vectors include, without limitations, pMAM, pDR2, pBK-RSV, pBK-CMV, poPRSV, and pOp13.

In another aspect, the invention provides kits for the at least partially reversible gene therapies. In different embodiments of the invention, the kits comprise any of the deoxyribonucleic acid sequences as described above. Additionally, the kit may comprise a set of instructions for efficient and safe use of the kit. A person skilled in the art will undoubtedly appreciate that the set of instruction may be provided in any medium, including, without limitations, printed, audio and video recorded, and electronic.

In additional embodiments of the invention, the kits further provide at least one sequence modifier, e.g., the first sequence modifier, or the second sequence modifier or a combination thereof. A person of ordinary skill in the art will understand that depending on the number and the character of flanking sequences in the provided deoxyribonucleic acid sequence of the present invention, that one or more sequence modifiers may be provided. For example, if the deoxyribonucleic acid sequence has only the loxP flanking sequences, then the sequence modifier is Cre. On the other hand, if the deoxyribonucleic acid sequence has both loxP and an attB/attP pair of flanking sequences, at least one sequence modifier is selected from the group consisting of Cre, ΦC31 and a combination thereof.

In additional embodiments, the sequence modifier may be conveniently formulated with one or more pharmaceutically acceptable diluents, excipients and/or carriers. Such formulations may be advantageous for storage of the at least one sequence modifier.

In another aspect, the invention provides a host cell comprising the deoxyribonucleic acid sequence, as described above. A person of ordinary skill would understand and appreciate that a wide variety of cell types are suitable for this aspect of the invention. These cell types include, without limitation, neurons, skeletal myocytes, cardiac myocytes, smooth muscle cells, endocrine cells, adipocytes, white blood cells, epithelial cells, glial cells, renal cells, corneal cells, bone marrow cells, hepatocytes, endothelial cells, angioblasts, cardiac myoblasts, vascular smooth muscle cells, periosteal cells, perichondrial cells, fibroblasts, skeletal myoblasts, neuronal cells, epidermal cells, non-vascular endothelial cells, keratinocytes, basal cells, lung cells, immune system cells, ovarian cells, cervical cells, foreskin cells, and totipotent, multipotent, or pluripotent cells, (including, without limitation, embryonic and adult stem cells), and any combination thereof. In one embodiment, the host cell comprises a stem cell. The stem cells may be derived, for example, from hone marrow, glial cells, and adipose tissues.

A person of ordinary skill in the art will undoubtedly recognize the advantages of this aspect of the invention, most notably, that the host cell may be maintained in culture. Thus, it would be easier and more efficient to transform the host cell with the at least partially reversible gene therapy system of the practitioner's choice. In addition, transforming the host cell in culture before administering the host cell to the patient has the advantage of allowing the practitioner to verify and quantify the level of expression of the therapeutic gene in the host cell and also verify the reversibility of the gene therapy in the host cell upon contacting the host cell with the appropriate sequence modifier (such as Cre recombinase, FLP recombinase, or phiC31 recombinase or combinations thereof.

A person of ordinary skill in the art would further recognize that it would be advantageous to select cells which are immunologically compatible with the patient's immune system (i.e., will not trigger an immune response). The host cells according to this embodiment of the invention may be obtained from the patient himself or from tested cell donors, including, without limitation, the patient's relatives, or other suitably qualified and consenting donors that are living or recently deceased.

As mentioned above, the host cells can be maintained in culture. The protocols for maintaining cells in culture are well known in the art and described, for example, in Basic Cell Culture Protocols, Jeffrey W. Pollard and John M. Walker (Editors), Humana Press, $2^{nd}$ Ed. 1997.

A person of ordinary skill in the art will further recognize that at least some of the cell types suitable to be host cells may not only be maintained but also differentiated in culture. The cells may be maintained and/or differentiated, for example, by adding to the culture media an agent that promotes the growth or differentiation of the cultured cells. For example, it has been known in the art that mesenchymal stem cells can differentiate into mesodermal lineage cells such as osteocytes, chondrocytes, adipocytes and myocytes. Further, these cells may differentiate into neurons and neuroglial cells, U.S. Pat. Pub. 20060099190 (Suh). Further, it has been reported that embryonic stem cells may be differentiated into insulin-secreting cells by culturing these cells in a first media containing Activin A and then culturing these cells in a second media containing nicotinamide. U.S. Pat. No. 7,033,831.

The invention further provides a method of at least partially reversible gene therapy comprising administering to a patient at least one host cell described above. As also discussed above, it is advantageous that the at least one host cell may be obtained from immunologically compatible sources, such as the patient him- or herself, the relatives and the tested donors.

The targeted area for the injection of the host cells may be located by the same techniques useful for location of the targeted areas for injecting the at least partially reversible gene therapy system of the present invention, as described above.

It has been previously shown that gene therapy vectors, such as, for example, AAV vectors, are capable of retrograde axonal transport to introduce and express genes in neurons. U.S. Patent Pub. 20030118552 (Kasper). Thus, in another aspect, the invention provides a method and a system for a transient mapping of neuronal pathways.

Such method and system can be used in combination with the at least partially reversible gene therapy system of the present invention. Accordingly, the use of such methods and systems will allow the practitioner to activate gene therapy only after the accuracy of the injection of the at least partially gene therapy system of the present invention has been verified thus providing an additional safeguard for using the system of the present invention. For example, in one embodiment, the at least partially reversible gene therapy of the present invention will comprise, in addition to the parts described above, a marker sequence. In another embodiment, the bioactive sequence (e.g., the first bioactive sequence or at least the second bioactive sequence) may comprise the marker sequence. Thus, the practitioner can verify the correct placement and/or distribution of the at least partially reversible gene therapy system of the present invention prior to initiating the gene therapy treatment. One non-limiting embodiment allowing for such control can be as follows from 5' to 3':

the first member of the first pair of the flanking sequences;
a first tissue-specific promoter;
the first member of the second pair of the flanking sequences;
a constitutively active promoter;
a first bioactive sequence comprising a marker sequence under operable control of the constitutively active promoter;
the second member of the second pair of the flanking sequences;
at least the second bioactive sequence;
the second member of the first pair the flanking sequences.

A person of ordinary skill in the art will undoubtedly recognize that if the partially reversible gene therapy system described in the previous paragraph is administered to a patient, the second bioactive sequence will not be immediately expressed, but the marker protein will be. Thus, the practitioner will have an opportunity to verify the correct location/distribution of the partially reversible gene therapy system. If the location is correct, the practitioner will add the second sequence modifier to remove the sequence between the second pair of flanking sequences and place the second bioactive sequence under the control of the tissue-specific promoter and allow for expression of the gene therapy compound.

On the other hand, if the gene therapy system is placed or distributed incorrectly, the practitioner has an option of adding at least the first sequence modifier to remove both the marker sequence and the second bioactive sequence, and thus completely inactivate the gene therapy system. The removal of these components of the gene therapy system can be verified by visualization techniques, such as, for example, MRI.

Further, this invention provides a system and a method allowing for a verification that the at least one sequence modifier successfully removed the desired sequence (i.e., the first bioactive sequence), thus allowing the practitioner to stop administering the at least one sequence modifier when it is no longer necessary. This is important as a safety consideration for the patient because it is known that prolonged exposure of cells to some sequence modifiers, such as PhiC31, can cause chromosomal aberrations in cells (see Jeppesen, I., Nielsen, K., and Jensen, T. G. PhiC31 integrase induces chromosomal aberrations in primary human fibroblasts, *Gene Therapy*, 2006 (13) 1188-1190.)

In this embodiment, the desired sequence (i.e., the sequence between the member of the first pair of the flanking sequences) comprises both a marker sequence and a therapeutic sequence (e.g., a siRNA, or an shRNA). The marker sequence can be operably linked to the same or another regulatory sequence as the therapeutic sequence. Administering of the first sequence modifier will remove both the marker sequence and the therapeutic sequence.

The invention will now be described in the following non-limiting examples.

EXAMPLES

Example 1

Transgenic Mice Model

The inventors used the BAG transgenic mouse model of HD (BAC-HD) that expresses the full-length human mutant htt, with loxP sites (SEQ ID NO 125: 5'-ctacttcgta tagcatacat tatacgaagt tat-3', SEQ. ID NO 126: 5'-ataacttcgt atagcataca ttatacgaag ttat-3') flanking the exon 1 of mutant htt sequence encoding 97 CAC. This BAC transgenic mouse model exhibits progressive behavioral and neuropathological impairments (Gray et al., 2008, *J. Neurosci.*, 28:6182-95).

Example 2

Treatments

Two-month-old wildtype (Wt) and transgenic (Tg) BAC-HD mice were stereotaxically injected in groups of 18 (9 males, 9 females) with 5 μl of pre-validated AAV2/1 constructs (expressing Cre) ($10^9$ virus expressing generics) into the striatum of both hemispheres at a rate of 0.5 μl/min.

CRE delivered in the striatum of BAC-HD mice as a prelude to deciphering the potential therapeutic benefit of RNAi-mediated knockdown of mutant htt in HD. The coordinates for injection were +0.5 mm (anterior-posterior); +1.8 mm (medial-lateral), and −3.6 mm (dorsal-ventral), relative to Bregma.

In addition, the inventors investigated the therapeutic potential of supplementing brain-derived neurotrophic factor (BDNF) protein the striatal reduction of which is also implicated in the pathogenesis of HD. BDNF was administered intrastriatally as a nucleic acid sequence within AAV in the amount of $10^9$ genomes.

Thus, the treatment groups were as follows: Inert (AAV expressing a control sequence); Cre (AAV expressing Cre); Cre+BDNF.

All behaviors were assessed blind, 1 week prior to treatment and intermittently until 12 months of age (ongoing).

All statistical analyses were performed using 2-way repeated measures anova followed by Tukey's post-hoc test.

Example 3

Treatment with Cre Alone and with a Combination of CRE and BDNF Reverses Motor Deficit in Tg BAC-HD Mice Mice were first trained to traverse a circular beam (2-5 cm diameter, 40 cm length) from one end that was lit by a 60 W bulb to another end that terminated into a dark box.

Immediately after completion of training (5 successful trials on the training beam), mice were tested on four beams that presented an increasing challenge to traverse (1.2 cm through 0.3 cm diameter). The number of footslips, total distance traveled, and total time taken to traverse all beams were scored blind; data are represented as mean±SEM values for each group. A fall was scored with cut-off values of 4 for the number of footslips and 20 sec for the time to traverse per beam.

As demonstrated in FIG. 1, control Tg BAC-HD mice exhibited a higher number of footslips compared to wt animals at all three time points (2 months, 5 months, and 8 months). Treatments with Cre or Cre+BDNF significantly reduced the number of footslips in five ($p<0.001$, Tg-Cre vs. Tg-inert; $p<005$ Tg-Cre+BDNF vs. Tg-inert) and eight-Month old Tg BAC-HD mice ($p<0.01$, Tg-Cre vs. Tg-inert; $p<0.001$, Tg-Cre BDNF vs. Tg-inert). When compared to the wt mice, the number of footslips in five and eight month-old Tg BAC-HD mice treated with Cre or Cre+BDNF was not significantly different from that of the control wt mice or wt mice treated with Cre (Tg-Cre or Cre+BDNF vs. Wt. Cre or inert; all nonsignificant at 5 or 8 month time point).

Figure 2:
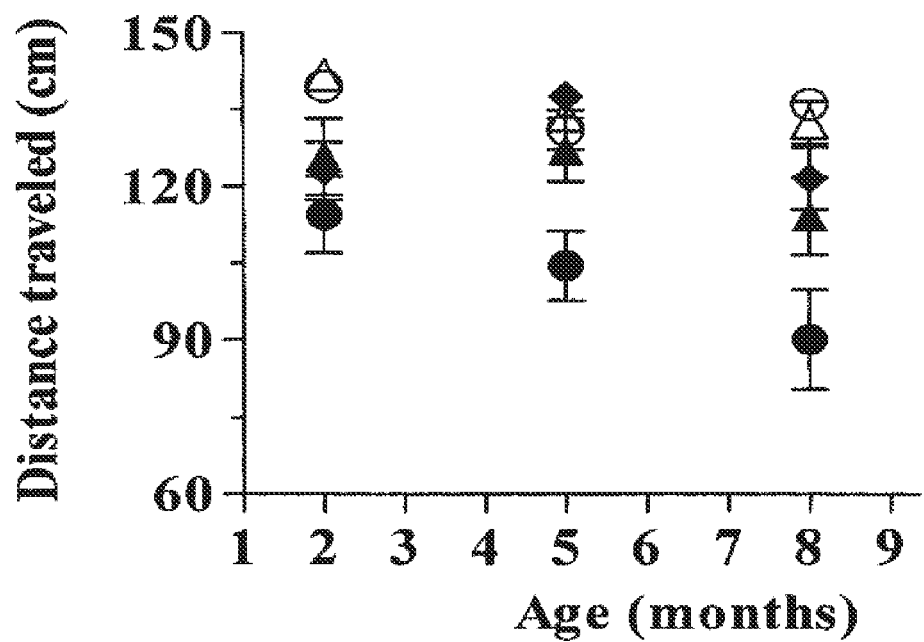
FIG. 2 illustrates the increase of distance traveled at five and eight months of age by transgenic (Tg BAC-HD) mice treated with Cre or Cre+BDNF at 2 months of age, and trained to traverse a circular beam.

The distance traveled by the animals in this experimental set-up is summarized in FIG. 2. Control Tg BAC-HD mice traveled a shorter distance than the wt animals, and the difference between the Tg BAC-HD and wt mice increased at five and eight months. Treatments with Cre or Cre+BDNF significantly increased the distance traveled in five ($p<0.05$, Tg-Cre vs. Tg-inert; $p=0.001$, Tg-Cre+BDNF vs. Tg-inert) and or eight-month old Tg BAC-HD mice ($p<0.05$, Tg-Cre vs. Tg-inert; $p<0.001$, Tg-Cre+BDNF vs. Tg-inert) compared to the control transgenic animals. When compared to the wt mice, five and eight month-old Tg BAC-HD mice treated with Cre or Cre+BDNF traveled about the same distance as the control wt mice or wt mice treated with Cre (Tg-Cre or Cre+BDNF vs. Wt. Cre or inert; all non-significant at 5 and 8 month time point).

Figure 3:
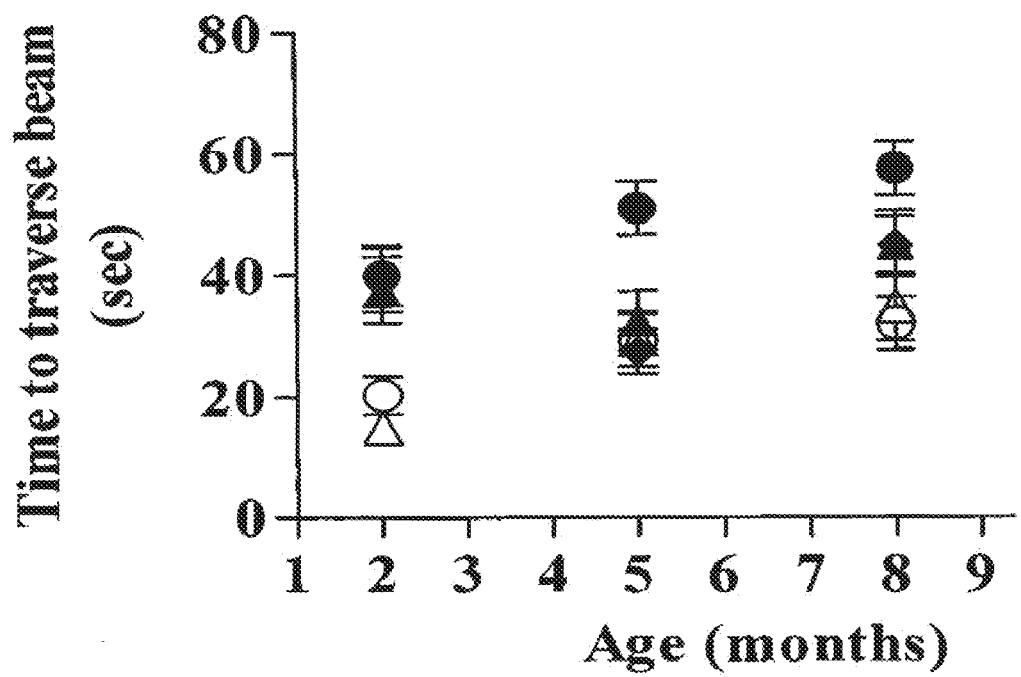
FIG. 3 illustrates decrease in the time to traverse the beam at five and eight months of age by transgenic (Tg BAC-HD) mice treated with Cre or Cre+BDNF at 2 months of age.

FIG. 3 illustrates the time taken by the animals to traverse the beam. While differences between wt and transgenic mice were observed in two-month old animals, treatment with Cre or Cre+BDNF at two months age attenuated or eliminated these differences at five ($p<0.01$, Tg-inert vs. Wt-inert or Wt-Cre or Tg-Cre+BDNF; $p<0.05$, Tg-inert vs. Tg-Cre) and eight months of age ($p<0.001$, Tg-inert vs. Wt-inert; $p<0.01$, Tg-inert vs. Wt-Cre).

Example 4

Figure 4:
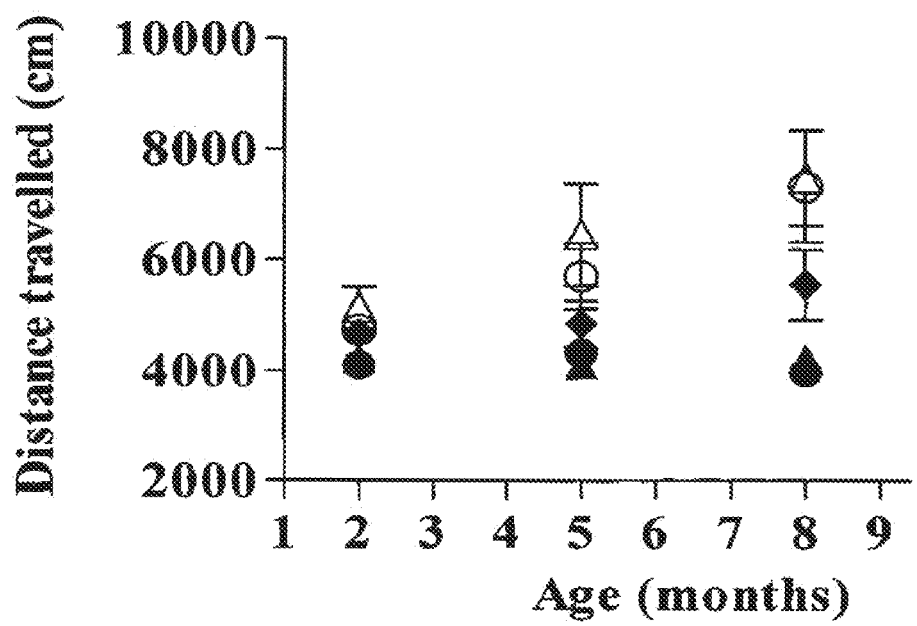
FIG. 4 illustrates an improvement of locomotor activity in Tg BAC-HD mice upon treatment with AAV-Cre+AAV-BDNF.

Tg BAC-HD Mice Reveal Improved Locomotor Activity Upon Treatment with AAV-Cre AAV-BDNF, while their Deficit in the Accelerating Rotarod Test Remains Unaltered Mice were placed in an open field chamber (40 cm×40 cm), and the distance traveled was scored by the ANY-Maze software (Stoelting, Wood Dale, Ill.). Data are presented in FIG. 4 as mean±SEM values for each group. Briefly, the distance traveled increased with age in wt animals. In two month old Tg BAC-HD mice, the distance traveled was about the same as in wt animals. However, as the transgenic mice aged, the distance did not change. In eight month old control transgenic animals, the distance traveled was significantly less than the distance traveled by age-matched wt counterparts ($P<0.001$, Tg-inert or Cre vs. Wt-inert or Cre). Treatment with Cre+BDNF, but not Cre alone, somewhat increased the distance traveled, albeit no statistically significant differences were observed.

Figure 5:
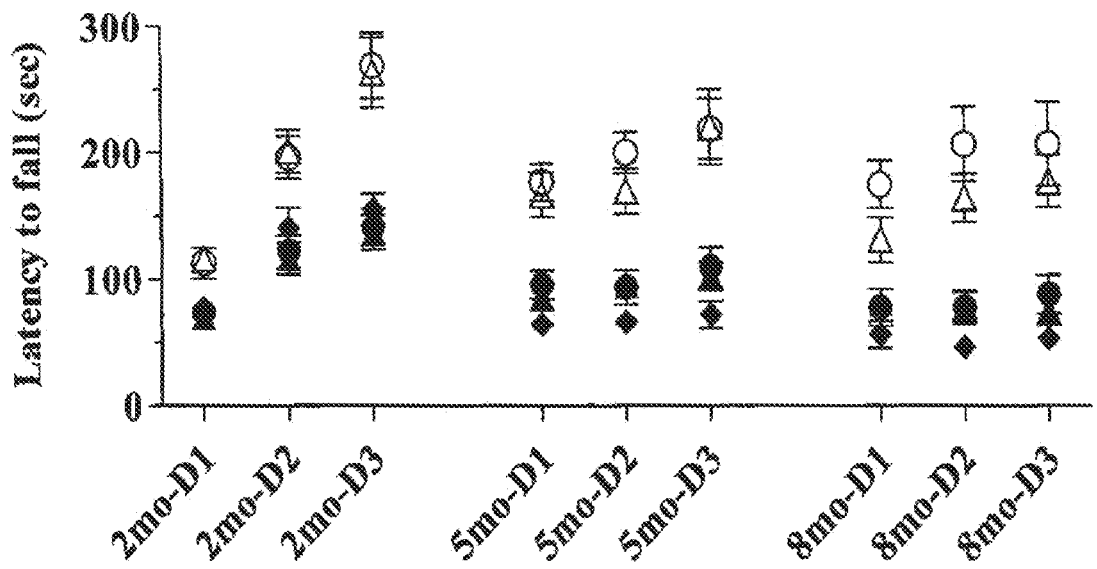
FIG. 5 demonstrates that treatment of Tg BAC-HD mice, with AAV-Cre+AAV-BDNF does not affect performance in the accelerating rotarod test.

In another test, mice were subjected to an accelerating rotarod test (acceleration from 4-40 rpm for 5 min, followed by 40 rpm for 5 min) for 3 days, involving 3 trials (separated by an hr) per day. The latency to fall per day has been depicted in FIG. 5 as mean±SEM values for each group. In this test, treatments with Cre or Cre+BDNF did not improve the deficit exhibited by transgenic mice compared to wt animals.

Example 5

Figure 6:
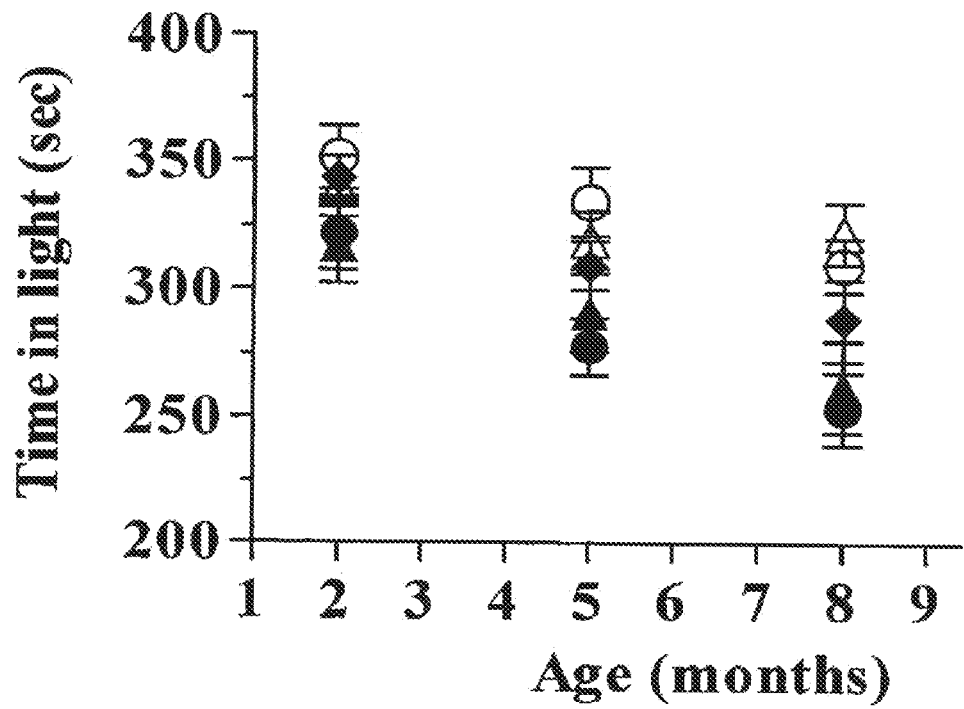
FIG. 6 demonstrates that Tg BAC-HD mice treated with Cre+BDNF tend to demonstrate a reduced anxiety.

Ongoing Testing Indicates Possibly Reduced Anxiety in the Tg BAC-HD Mice Upon Treatment with Cre+BDNF Mice were placed in the center of the light compartment facing away from the dark compartment in the light-dark box, and the number of transitions across the two compartments, total time spent in the light compartment, and the latency to first enter the dark compartment were scored blind. These data are illustrated in FIG. 6. ($p<0.05$, Tg-inert or Cre vs. Wt-inert or Cre at 8 months age). The mean±SEM values are presented for the time spent in light by each group; no group differences were observed for the number of transitions and latency to enter the dark compartment at any age.

Example 6

Figure 7:
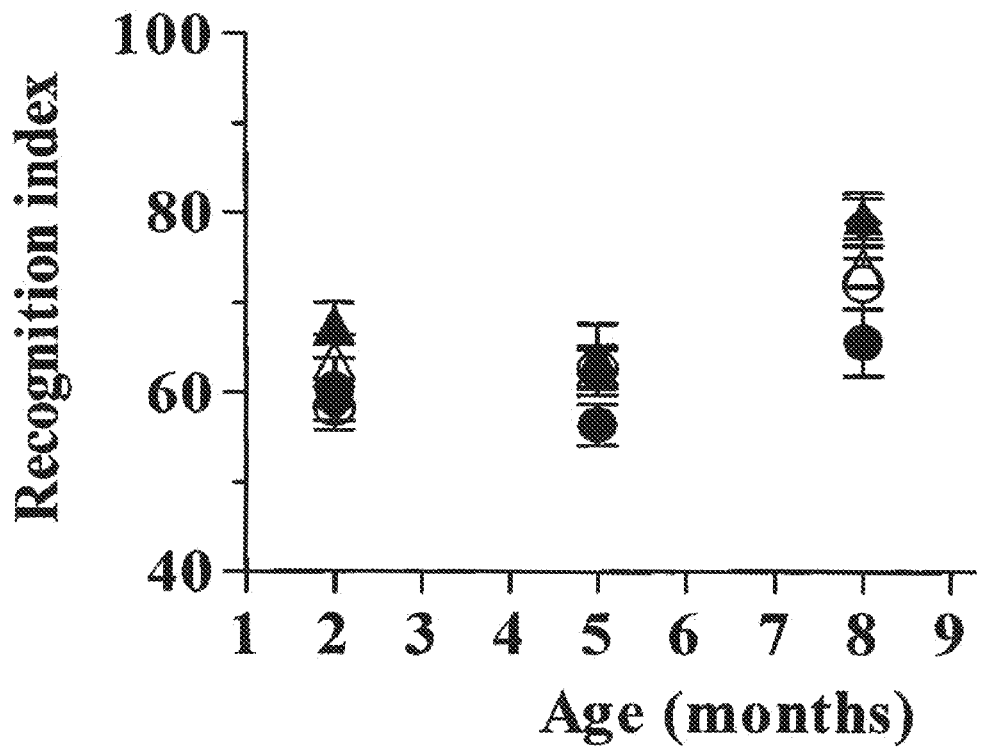
FIG. 7 demonstrates that treatment with Cre with or without BDNF tends to improve the performance of Tg BAC-RD mice in the novel object recognition test.
Figure 8:
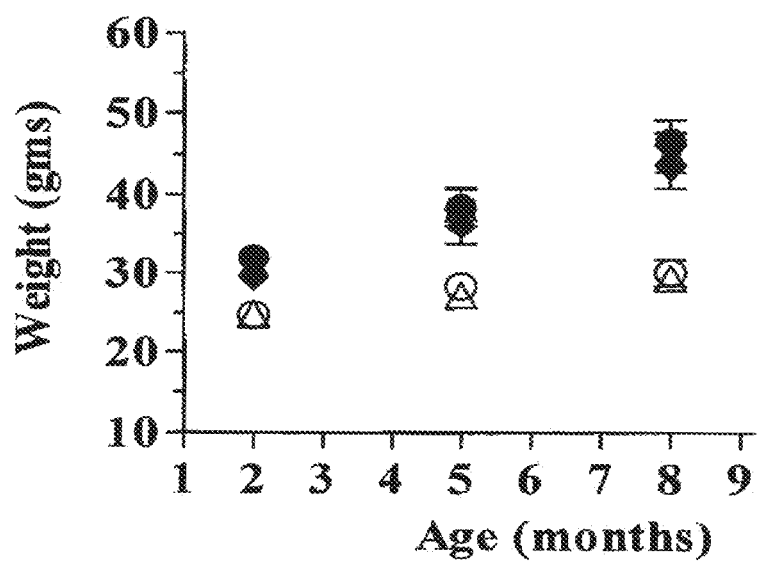
FIG. 8 demonstrates that Tg BAC-HD mice progressively gain weight as compared to wt animals.

Cre±BDNF Tends to Improve the Performance of Tg BAC-HD Mice in the Novel Object Recognition Test The novel object recognition test was continued on mice following the locomotion task in the open-field chamber. Mice were first allowed to explore 2 different objects, placed diagonally opposite in the field, for 10 min. In the subsequent 10-min trial one of the objects was replaced with a novel object, and the recognition index was calculated as described (Dodart et al., 2002, *Nat. Neurosci.*, 5:452-7) using the ANY-maze software (Stoelting). Data are presented in FIG. 7 as mean±SEM values for each group. ($p<0.01$, Tg-inert vs. Tg-Cre or Cre+BDNF at 8 months age).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

All publications cited in the specification, both patent publications and non-patent publications, are indicative of the level of skill of those skilled in the art to which this invention pertains. All these publications are herein fully incorporated by reference to the same extent as if each individual publication were specifically and individually indicated as being incorporated by reference.

The invention claimed is:

1. A deoxyribonucleic acid (DNA) sequence comprising:
   (1) a first sequence, said first sequence having a 5' end and a 3' end; and
   (2) a second sequence, said second sequence having a 5' end and a 3' end; and
   (3) a first pair of flanking sequences, wherein a first member of the first pair is located upstream of the 5' end of the first sequence and a second member of the first pair is located downstream of the 3' end of the second sequence; and
   (4) a second pair of flanking sequences, wherein a first member of the second pair is located downstream of the 3' end of a first member of the first pair and upstream of the 5' end of the first sequence; and a second member of the second pair is located downstream of the 3' end of the first sequence and upstream of the 5' end of the second sequence; wherein:
   one of the first sequence or the second sequence encodes a siRNA or shRNA capable of reducing mutated huntingtin and the other of the first sequence or the second sequence encodes a brain-derived neurotrophic factor (BDNF),
   the first sequence is excisable from said deoxyribonucleic acid sequence upon exposure of said deoxyribonucleic acid sequence to a second sequence modifier that recognizes the second pair of flanking sequences, and either:
   a) the second sequence is excisable from said deoxyribonucleic acid sequence upon exposure of said deoxyribonucleic acid sequence to a first sequence modifier that recognizes the first pair of flanking sequences, or
   b) both the first and second sequences are excisable together from the said deoxyribonucleic acid sequence upon exposure of said deoxyribonucleic acid sequence to the first sequence modifier; and
   wherein the first member of the first pair of flanking sequences is located upstream of the 5' end of the first member of the second pair.

2. The DNA sequence of claim 1, wherein said siRNA or shRNA is capable of reducing mutated huntingtin in an allele-specific manner and comprises a first strand and a second strand, each of said strands being 19-29 nucleotides long, and wherein the first strand comprises a sequence encoding SEQ ID NO: 65.

3. The DNA sequence of claim 1, wherein:
   the first sequence modifier is different from the second sequence modifier;
   the first sequence modifier is selected from the group consisting of Cre recombinase, FLP recombinase, and phiC31 recombinase; and the second sequence modifier is selected from the group consisting of Cre recombinase, FLP recombinase, and phiC31 recombinase.

4. The DNA sequence of claim 1, included within a viral vector.

5. The DNA sequence of claim 4, wherein the viral vector is an AAV vector.

6. The DNA sequence of claim 1, wherein the first or second sequence is operably linked to a regulatory sequence.

7. The DNA sequence of claim 6, wherein the regulatory sequence is a promoter.

8. The DNA sequence of claim 7, wherein the promoter is a constitutively active promoter.

9. The DNA sequence of claim 7, wherein the promoter is a tissue- or organ-specific promoter.

10. The DNA sequence of claim 7, wherein the promoter is one selected from the group consisting of a cytomegalovirus (CMV) promoter, a SV40 early promoter region, a Rous sarcoma virus (RSV) promoter, a herpes thymidine kinase (TK) promoter, a chicken beta-actin promoter, a RNA polymerase III promoter, a MMLV-LTR promoter, and an EF1α promoter.

11. The DNA sequence of claim 10, wherein the RNA polymerase III promoter is one selected from the group consisting of U6, H1, 7SK and 7SL promoters.

* * * * *